US007258863B2

(12) United States Patent
Oaks et al.

(10) Patent No.: US 7,258,863 B2
(45) **Date of Patent: *Aug. 21, 2007**

(54) HETEROLOGOUS PROTECTION INDUCED BY IMMUNIZATION WITH INVAPLEX VACCINE

(75) Inventors: Edwin V. Oaks, Gambrills, MD (US); Kevin R. Turbyfill, Odenton, MD (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 42 days.

This patent is subject to a terminal disclaimer.

(21) Appl. No.: 10/150,814

(22) Filed: May 17, 2002

(65) Prior Publication Data

US 2002/0197276 A1 Dec. 26, 2002

(51) Int. Cl.
*A61K 39/385* (2006.01)
*A61K 39/02* (2006.01)

(52) U.S. Cl. .............................. 424/197.11; 424/234.1; 530/825

(58) Field of Classification Search ........... 424/197.11; 530/350, 388.1
See application file for complete search history.

(56) References Cited

U.S. PATENT DOCUMENTS

| | | | | |
|---|---|---|---|---|
| 6,245,892 | B1 | 6/2001 | Oaks | 424/282.1 |
| 6,248,329 | B1 * | 6/2001 | Chandrashekar et al. | 424/191.1 |
| 6,277,379 | B1 * | 8/2001 | Oaks et al. | 424/197.11 |

FOREIGN PATENT DOCUMENTS

| | | |
|---|---|---|
| WO | WO 00/18354 | 4/2000 |

OTHER PUBLICATIONS

Turbyfill et al., Infection and Immunity vol. 68, No. 13, pp. 6624-6632, Dec. 2000.*
Alexander et al (Vaccine, 14(11):1053-1061, 1996).*
Ellis, R.W. (Chapter 29 in "VACCINES" Plotin, S.A. et al eds, W. B Saunders Co., Philadelphia, PA, 1988, p. 571, second full paragraph.*
Jennison et al, FEMS Microbiological Reviews, 28:43-58, 2004.*
Charkrabarti et al (Acta Paediatr, 88:161-5, 1999).*
Turbyfill et al. (1998) Identification of Epitope and Surface-Exposed Domains of *Shigella flexneri* Invasion Plasmid Antigen D (IpaD). *Infection and Immunity* 66, 1999-2006.
Barzu et al. (1996) Induction of a Local Anti-IpaC Antibody Response in Mice by Use of a *Shegella flexneri* 2a Vaccine Candidate: Implications for Use of IpaC as a Protein Carrier. *Infection and Immunity* 64, 1190-1196.
Turbyfill et al, "Isolation and Characterization of the *Shigella* Invasin Complex and Use as a New Subunit Vaccine," Abstracts of the General Meeting of the American Society for Microbiology, vol. 99, May 30, 1999, p. 291.
Oaks et al, "Evaluation of the *Shigella* Invasin Complex and Purified IpaC as Mucosal Adjuvants," Abstracts of the General Meeting of the American Society for Microbiology, vol. 99, 1999, p. 282.

* cited by examiner

*Primary Examiner*—Patricia A. Duffy
(74) *Attorney, Agent, or Firm*—Elizabeth Arwine

(57) ABSTRACT

In this application is described a composition, Invaplex, derived from a gram negative bacteria for use in generating an immune response in a subject against one or more heterologous species or strains of gram-negative bacteria.

3 Claims, 21 Drawing Sheets

PROTECTIVE CAPACITY OF MONOVALENT AND BIVALENT INVAPLEX VACCINES AGAINST CHALLENGE WITH S. FLEXNERI OR S. SONNEI

Weight Loss and Recovery in Invaplex-Immunized Mice Infected with S. flexneri or S. sonnei

- ■ 24 flex/flex chall
- ● 50 son/son chall
- ▲ 24 flex/son chall
- ◇ 50 son/flex chall
- □ saline/flex chall
- ○ saline/son chall
- △ control Protective Effect of Invaplex Vaccines Against Homologous and Heterologous Challenge Serum IgG levels to S. flexneri LPS in mice immunized with monovalent Invaplex vaccines anti sonnei lps IgA monovalent vaccines water extract IgA, vir+, monovalents Water extract,vir-,IgA Cross-reactive antigens common to Invaplex 50 from *Shigella* spp. and Enteroinvasive *E. coli*

Cross-reactive antigens common to Invaplex 50 from *Shigella* spp. and Enteroinvasive *E. coli*

*S. sonnei* Invaplex 50 stimulates antibodies in guinea pigs which recognize protein antigens present in *Shigella* species and enteroinvasive *E. coli*.

*S. flexneri* 2a Invaplex 50 stimulates antibodies in guinea pigs which recognize protein antigens present in all *Shigella* species and enteroinvasive *E. coli*

Identification of cross-reactive protein antigens of Invaplex 50 on the surface of shigellae

HETEROLOGOUS PROTECTION INDUCED BY IMMUNIZATION WITH INVAPLEX VACCINE

INTRODUCTION

Shigellosis is a leading cause of human diarrheal disease. It has been estimated that over 160 million cases occur annually, particularly in developing countries, with over 1 million cases resulting in death (Kotloff et al., 1999, WHO 77, 651–666). The most prevalent *Shigella* species causing disease are *S. flexneri, S. sonnei*, and *S. boydii*. In industrialized countries it is estimated that there are approximately 1.5 million cases of shigellosis per year (Kotloff et al. 1999, supra). The low incidence of shigellosis in industrialized countries implies that the adult population is non-immune and susceptible. This becomes readily apparent when American troops or travelers are deployed to areas endemic for *Shigella*. Although antibiotics are effective against bacillary dysentery, the constant emergence of antibiotic resistance in *Shigella* spp. (Hoge et al., 1998, Clin. Infect. Dis., 26:341–345), even to the newest antibotics, underscores the need for an effective vaccine to help control *Shigella* disease.

The pathogenesis of *Shigella* is attributed to this organism's ability to invade, reside, and replicate intracellularly within the colonic epithelium. The invasion of host cells by *Shigella* spp. is a complex multifactorial event in which many different bacterial proteins are involved. Many of the genes for key *Shigella* virulence proteins are encoded on a large 140 Mdal plasmid. Several of the plasmid encoded proteins called the invasion plasmid antigens (IpaA, IpaB, IpaC, and IpaD proteins) (Buysse et al., 1987*, J. Bacteriol.* 169, 2561–2569) are essential virulence factors. Similar proteins, called Sip proteins, are made by members of the genus *Salmonella* (Kaniga et al, 1995*, J. Bacteriol.* 95, 3965–3971). Upon contact or attachment to host cells, the *Shigella* invasins induce a phagocytic event which results in engulfment and internalization of the bacterium by the host cell. Recent reports have identified that IpaB and IpaC form a complex that can be found in the growth medium of *Shigella* cultures (Menard et al, 1998*, EMBO J* 13, 5293–5302; Watari et al 1995*, EMBO J* 14, 2461–2470). The components of this complex are involved in the invasion process, but the actual mechanisms have not been defined (Menard et al, 1994*, Cell* 79:515–525). In addition, purified IpaC has been shown to bind to host cells and participate in the uptake of avirulent shigellae by host cells (Marquart et al., *Infect Immun.* 64:4182–4187, 1996). IpaB, IpaC and IpaD, along with LPS are known major antigens that infected individuals respond to after infection with shigellae (Li et al. 1993*, Scand. J. Infect. Dis.* 25, 569–577; Oaks et al, 1986*, Infect. Immun.* 53, 57–63; van DeVerg et al 1992*, J. Infect. Dis.* 166, 158–161). Monkeys or humans infected with shigellae produce antibodies predominantly to IpaB and IpaC, and also produce antibodies at high frequencey to IpaA, IpaD and VirG (another plasmid encoded virulence protein involved in intercellular spreading) (Oaks et al, 1986, supra).

These inflammatory and specific immune responses produced as a result of the *Shigella*-host interactions are likely directed at essential virulence components in an attempt to neutralize and eliminate the pathogen. The resulting immunity offers protection against future infection with the homologous serotype (Ferreccio, 1991 Am. J. Epidemiol., 134:614–627; Formal et al., 1991, J. Infect. Dis. 164: 533–537). Although the function of antibodies to the Ipa proteins is not entirely understood, it is possible to inhibit the invasiveness of *Shigella* or EIEC with monoclonal antibodies to IpaC or IpaB (Mills et al., 1988, Infect. Immun., 56:2933–2941, Shaikh et al., 1995, FEMS Microbiol. Lett., 125:247–253) and more recently a Mab to the carboxy-terminal end of IpaC exhibited inhibition of IpaC-induced actin polymerization in permeabilized host cells (Van Nhieu et al., 1999, EMBO J., 174:1990–2001). Epitope mapping of IpaC has indicated that infected monkeys responding to three epitopic regions are less likely to develop severe disease (Turbyfill et al, 1995 Infect. Immun. 63:3927–3935) and one of these three epitope regions (region III) co-localizes with the actin polymerization domain (Van Nhieu 1999, supra). Even so it has not been possible to correlate protective immunity with a specific antibody response to any of the invasins as measured by western blots or ELISAs. In contrast, numerous studies have concluded that LPS is an essential vaccine component (Ferreccio, 1991 supra; Formal 1991, supra; Mallett et al., 1995, Infect. Immun., 63:2382–2386; Orr et al., 1993, Infect. Immun., 61:2390–2395; Phalipon et al., 1995, J. Exp. Med., 182: 769–778) but is is also clear that LPS delivered by itself is not protective (Adamus et al., 1980, Infect. Immun., 30:321–324; Mallet 1995, supra). This suggests that presentation of LPS in a manner which elicits a protective immune response comparable to natural infection is necessary for a successful *Shigella* vaccine. However, vaccines dependent on only LPS for a protective immune response to *Shigella*, although effective against a homologous challenge, are limited in their potential to protect against heterologous *Shigella* species making it necessary to combine monovalent vaccines to create a multivalent vaccine. Unfortunately, due to the preponderance of *Shigella* serotypes, with apparent insignificant cross-protection, it has been difficult designing a broadly reactive LPS-based *Shigella* vaccine.

Our approach has been to use Invaplex, a subcellular vaccine composed of LPS and protein antigens of *Shigella*, including Ipa proteins, in a native virulence structure. Invaplex delivers essential antigens to the mucosal immune system and thereby stimulates a protective immune response (without an adjuvant) against infection with a *Shigella* strain from which the Invaplex was isolated. The immune response generated mimics a natural infection in that antibodies to LPS and the invasins are produced (Turbyfill & Oaks, 2000, Infection and Immunity 68, 6624–6632). While conducting experiments with bivalent Invaplex vaccines, we were surprised to discover that Invaplex 50 can provide protection against infection with a heterologous gram negative bacteria, i.e. a gram negative bacteria different than the source of the Invaplex. This is the first demonstration of *Shigella* vaccine protective against heterologous strains of gram negative bacteria.

Isolation and purification of Invaplex and its use as a vaccine against infection with the homologous bacteria, i.e. the bacteria from which the Invaplex was prepared, is described in U.S. Pat. Nos. 6,245,892 and 6,277,379, the content of which is hereby incorporated in its entirety.

Briefly, Invaplex was isolated during initial experiments aimed at isolating and purifying IpaC from a water extract of *Shigella*. Usually, IpaC is extracted from growth culture medium. We chose to use the water extract, i.e. the solution resulting from incubating the bacteria with shaking in sterile water, because we hypothesized that the quantity of IpaC would be greater in such an extract. To our knowledge, no protein involved in the invasiveness of gram negative bacteria had been previously isolated from a water extract of gram-negative bacteria. To our suprise, when water extract was subjected to various separation techniques such as gel filtration and ion-exchange chromatography, we found that whenever we could detect IpaC from the water extract we also detected IpaB, IpaD and LPS in the same fractions. We proceeded to design a method to isolate this complex and characterize it. The Invaplex preparations are isolated from virulent, invasive shigellae. A crude mixture is extracted from the shigellae with water. The water extract consists of many proteins and lipopolysaccharide (LPS). The water extract material is then applied to a FPLC ion-exchange column which resolves two key protein peaks, called Invaplex (invasin complex) 24 and Invaplex 50. Fractions containing Invaplex 24 and Invaplex 50 are collected. We found that the complex was composed of many proteins, including IpaB, IpaC, IpaD in addition to LPS. The Invaplex 24 and Invaplex 50 preparations containing Ipa proteins and the LPS form a structure in a completely native configuration and environment. Invaplex 50 also contains VirG*, and the previously undescribed 72 kDa and 84 kDa polypeptides. Unlike the Ipa proteins and VirG, the 72 kDa and 84 kDa polypeptides are not virulence plasmid encoded; nonetheless each Invaplex-associated protein is highly conserved among all *Shigella* species and thus represents broadly reactive antigens common to all *Shigella* species.

When Invaplex is used to immunize animals, it leads to an immune response directed against a native structure presented by gram-negative bacteria during infection. Mice and guinea pigs immunized with the Invaplex preparations showed a marked serum IgA and IgG response to several different antigens (including the water extract antigen, IpaC and LPS) present in the Invaplex 24 and Invaplex 50 preparations. The two Invaplex preparations were similar in that they both primed the mucosal immune system, but differed in the specificity of the immune response generated most likely due to antigen content differences. The animals were protected from challenge with homologous gram-negative bacteria by immunization with either Invaplex. Animals immunized with either Invaplex showed no visible signs of distress or toxicity.

In addition to its effectiveness as a vaccine, we found that the Invaplex product is also capable of delivering unrelated, admixed proteins, in a manner that enhances the immune response to these proteins. Thus, the *Shigella* Invaplex product has the potential to serve both as a vaccine for shigellosis and an adjuvant for other mucosal pathogens such as enterotoxigenic *E. coli* (ETEC) or *Campylobacter*.

Using the mouse lethal lung model, we have shown that Invaplex 24 and 50 from *Shigella flexneri* 2a are protective against homologous challenge. *S. sonnei* Invaplex 50 protected mice but *S. sonnei* Invaplex 24 did not, presumably due to its low quantities of LPS and Ipa proteins. Immunized animals (*S. flexneri* Invaplex 24 or 50, *S. sonnei* Invaplex 50) produced antibodies to LPS and the water extract proteins which is a response very similar to that occurring after a natural infection in humans. Mice immunized with *S. sonnei* Invaplex 24, which is deficient in LPS, IpaB and IpaC, did not produce detectable antibodies to the Ipa proteins or LPS. These results suggested that an effective Invaplex vaccine must have sufficient quantities of the invasins and LPS to stimulate a protective immune response.

Effective monovalent Invaplex vaccines were combined to make a successful bivalent *S. flexneri* 2a/*S. sonnei* vaccine. Mice immunized with a bivalent *S. flexneri* Invaplex 24/*S. sonnei* Invaplex 50 vaccine were protected from a lethal challenge of *S. flexneri* 2a (87% protection, $p<0.001$) or *S. sonnei* (100% protection, $p<0.001$). This level of protection was comparable to the monovalent components used for homologous protection. Mice immunized with the bivalent combination of *S. flexneri* Invaplex 24/*S. sonnei* Invaplex 50 developed serum IgA and IgG antibody responses to *S. flexneri* LPS, *S. sonnei* LPS and the water extract (vir+). This is very similar to that elicited by monovalent Invaplex vaccines. Neither the monovalent *S. flexneri* nor the monovalent *S. sonnei* Invaplex vaccines stimulated production of antibodies to the heterologous LPS.

As part of the above mentioned bivalent vaccine studies, groups of control mice immunized with either the *S. flexneri* Invaplex 24 or *S. sonnei* Invaplex 50, were challenged with the heterologous agent. For example, *S. flexneri* Invaplex 24 immunized mice were challenged with *S. sonnei*. In this experiment only 30% of the *S. flexneri* Invaplex 24 immunized mice survived a lethal *S. sonnei* challenge ($p=0.052$). However, surprisingly, mice immunized with *S. sonnei* Invaplex 50 were protected against a lethal challenge of *S. flexneri* (89% survived, ($p<0.001$) (See Table 1 below). Heterologous protection is not typically predicted for *Shigella* vaccines because LPS is considered to be the key target antigen for protective immunity and it is LPS which is the major antigenic difference between *Shigella* species. However the presence of conserved proteins, including IpaB, IpaC, 72 kDa and 84 kDa, which are present in all species of *Shigella*, may have played a crucial role in this cross-protective, heterologous immunity elicited by the *S. sonnei* Invaplex 50 vaccine.

SUMMARY

In this application is described a gram-negative vaccine, Invaplex 50, effective for protection against infection with homologous species of gram negative bacteria, i.e. species from which the Invaplex was prepared, and effective against infection with heterologous species of gram-negative bacteria, i.e. species which did not contribute to the Invaplex.

The potential advantages of the Invaplex vaccine include the following: a) Invaplex is a non-infectious material which can be extracted from any *Shigella* species or enteroinvasive *E. coli* without the need for genetic alterations; b) it is safe and efficacious when delivered by the intranasal route in small animals; c) it has the potential to stimulate broadly reactive heterologous immunity to multiple *Shigella* species; d) it can be used as a primary or secondary (booster) vaccine; e) a multivalent Invaplex vaccine can be easily manufactured and evaluated; f) due to the adjuvant-like properties of the Invaplex, it is capable of delivering antigens from other mucosal pathogens such as ETEC or *Campylobacter*, leading to a truly multivalent vaccine against enteric pathogens.

Therefore, it is an object of the present invention to provide a gram negative vaccine comprising LPS, IpaB, IpaC, IpaD, VirG, 72 kDa component of Invaplex 50, and 84 kDa component of Invaplex 50 from a gram negative bacteria serotype or strain in an amount effective to elicit protective antibodies in an animal to a homologous or heterologous gram negative bacteria and a pharmaceutically acceptable diluent, carrier, or excipient. The source of any of the vaccine components can be a natural source such as Invaplex 50 isolated from any *Shigella* spp., or a recombinant source for example by combining isolated recombinant proteins and LPS or portions thereof in their native configuration in the proper stoichiometric proportions. It is understood that the vaccine can comprise components from the same species or serotype or components derived from different species and serotypes of *Shigella* or gram negative bacteria.

Therefore, it is an object of the present invention to provide a *Shigella* vaccine comprising Invaplex from a *Shigella* species or serotype in an amount effective to elicit protective antibodies in a subject to a homologous *Shigella* species and/or one or more species or strains heterologous to the source of Invaplex; and a pharmaceutically acceptable diluent, carrier, or excipient.

It is another object of the present invention to provide a vaccine against gram-negative bacteria comprising Invaplex from one or more gram-negative bacteria in an amount effective to elicit protective antibodies in a subject to bacteria homologous or heterologous to the source of Invaplex; and a pharmaceutically acceptable diluent, carrier, or excipient.

It is another object of the present invention to provide a enteroinvasive *E. coli* (EIEC) vaccine comprising Invaplex 50 from EIEC in an amount effective to elicit protective antibodies in a subject to EIEC homolgous and heterologous strains; and a pharmaceutically acceptable diluent, carrier, or excipient.

It is still another object of the present invention to provide a method of preparing a vaccine protective against infection with a homologous or one or more heterolgous species or strain of gram-negative bacteria comprising isolating Invaplex 50 from a gram-negative bacteria.

Further objects and advantages of the present invention will be clear from the description that follows.

DETAILED DESCRIPTION

Figure 1:
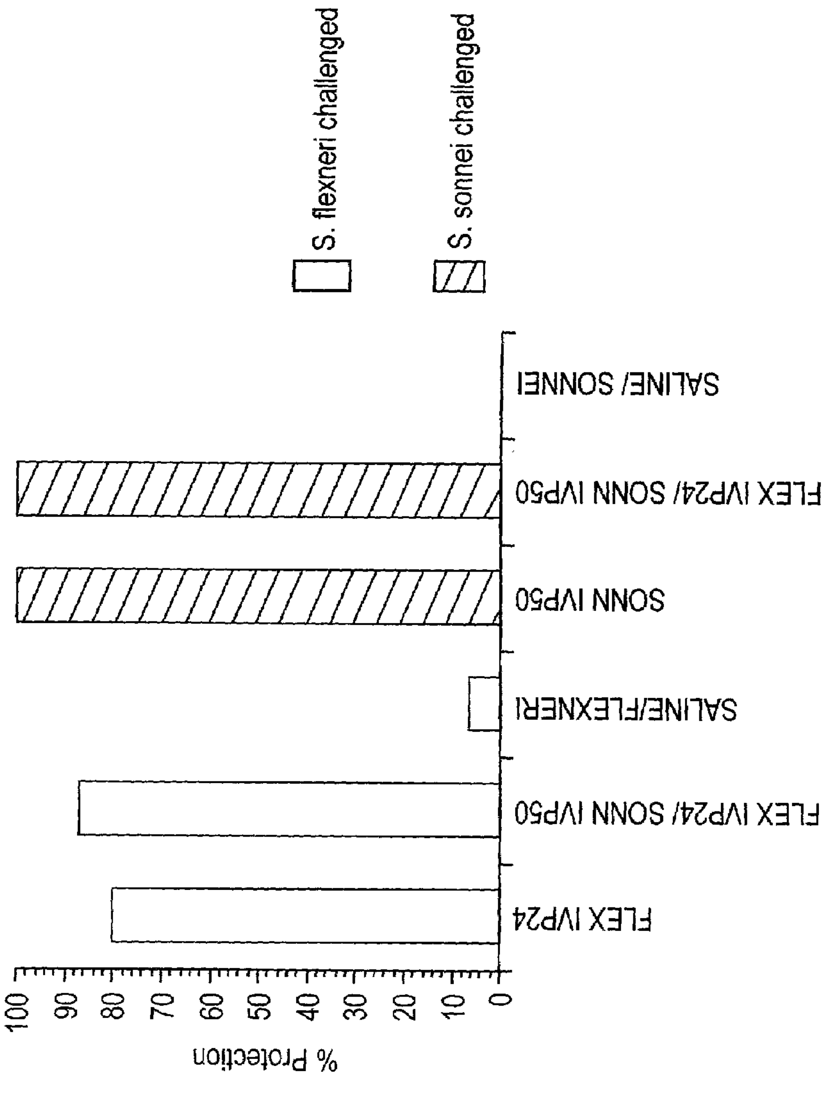
FIG. 1. Mice were immunized with either monovalent vaccines consisting of *S. flexneri* 2a Invaplex 24, *S. sonnei* Invaplex 50; the bivalent vaccine consisting of a mixture of *S. flexneri* 2a Invaplex 24 and *S. sonnei* Invaplex 50, or saline. The immunized and control mice were challenged intranasally with a lethal dose of *S. flexneri* 2a (3 groups on left side) or *S. sonnei* (3 groups on the right side). Infected mice were monitored for death up to 14 days after infection.

The present invention describes the use of Invaplex, comprising invasins in combination with the LPS complexed together to form a native structure, from one *Shigella* species as an immunogen protective against one or more heterologous species of *Shigella.*

The Invaplex can be prepared from any strain of gram negative bacteria for protection against infection with the bacteria from which the Invaplex was isolated and/or at least one other different strain, isolate, or species of gram negative bacteria. Gram negative bacteria, include but are not limited to, *Shigella flexneri, S. flexneri, S. sonnei, S. boydii, S. dysenteriae*, EIEC, *Salmonella* (including species *S. typhi, S. typhimurium*), *Yersinia* (*Y. pseudotuberculosis, Y. enterocolitica, Y. pestis*), enteropathogenic *E. coli, Rickettsia, Chlamydia, Brucella, Erhlichiae, Edwardsiella, Campylobacter* and *Neisseria*. These are all invasive bacteria that have a gram negative architecture (i.e. they have an inner or cytoplasmic membrane and an outer membrane surrounding the inner membrane).

In addition to wild type virulent gram negative bacteria, mutants of these organisms may be useful, such as those which hyper-express quantities of Ipa proteins and which might lead to the production of more Invaplex. Synthesis of the Ipa proteins is highly regulated in shigellae. The gene virF is involved in this regulation, as are other genes. (Sakai et al. 1988, *Mol. Microbiol.* 2, 589–597). All documents cited herein supra and infra are hereby incorporated in their entirety by reference thereto. Furthermore, it may be beneficial to prepare Invaplex from bacteria mutated in toxin genes so that the organism does not produce toxin, for example Shiga toxin. Invaplex prepared from tox− strains would be potentially safer because potential contamination by the toxin would be eliminated.

Increased levels of Invaplex may be achieved by extracting the complex in the presence of chemicals that stimulate secretion of the invasin proteins. Such chemicals include Congo Red, Evans Blue and direct orange (Bahrani, F. K,

*Infect Immun* 65:4005–4010, 1997). These chemicals could be added during the water extraction or during the growth of the bacteria.

In order to isolate the invasin proteins (Ipa proteins for *Shigella* or similar proteins in other invasive bacteria), the invasin proteins must be expressed by the bacteria. If the invasin proteins are not expressed on the surface or not expressed at all, the Invaplex will not be present. For example, in *S. sonnei* one must use form I cultures because they are virulent. Form II cultures do not express the Ipa proteins due to a large spontaneous deletion in the virulence plasmid. In addition, Invaplex may be isolated from bacteria to which genes encoding invasin proteins are added and expressed. Such bacteria may or may not previously contain and express invasin proteins and are chosen for a particular purpose such as ease of purification of Invaplex, or advantageous properties such as reduced toxin production.

Ipa protein presentation on the surface of shigellae may be decreased by mutating genes in the spa or mxi gene loci. The spa/mxi gene mutants make the Ipa proteins in normal quantities but the Ipa proteins are not presented or secreted to the exterior of the organism. Previously it has been shown that reduced amounts of IpaB and IpaC are in the water extract in spa mutants (Venkatesan et al., 1992, J. Bacteriol. 174, 1990–2001).

To overcome the possibility of using avirulent cultures, it is important that cultures used as a source of Invaplex be tested and proven to be virulent. This is usually done by the Sereny test (keratoconjunctivitis in guinea pigs as described in the Materials and Methods and Examples below). Another means in which to assure virulence is growing cultures of shigellae on Congo Red media in which colonies that are red (or bind the dye congo red) are almost always virulent. Assessment of virulence is extremely important with shigellae cultures as spontaneous mutations leading to avirulent cultures is commonplace. It is understood that even though some cultures may be partially virulent, it is possible to isolate Invaplex though the yield will be compromised.

In one embodiment, this invention relates to a method for isolating and purifying the Invaplex from gram-negative bacteria. The present method uses an improvement of the water extraction technique described by Oaks et al., 1986 (*Infect Immun* 53, 57–63). These improvements were designed to increase yield of functional product by minimizing the time to prepare the water extract preparation. The improvements include using an ion-exchange column capable of concentrating the Invaplex thereby eliminating the need to concentrate the water extract by time-consuming ultrafiltration step prior to loading onto the ion-exchange column. Ultrafiltration often took overnight to perform during which time proteolytic degradation might occur. The Ipa proteins are extremely labile and degrade rather quickly. Another improvement is the amount of water used to extract the proteins. The present method uses a volume of water which is 1/20 the volume of the medium used to grow the culture instead of a ratio of 1/10 used previously (Oaks et al., 1986, supra). For example if the shigellae are grown in 20 liters of medium than one would use 1 liter of water for the extraction. Other modifications include filtration of the water extract with a 0.45 or 0.22 um membrane both before and/or after ultracentifugation. This step will remove bacteria from the water extract material and make it less likely to contain viable bacteria. This step will be essential for any product to be used in human trials. Also the original procedure described in Oaks, 1986 (supra) used PMSF (phenylmethylsulfonyl fluroide) a very potent and dangerous protease inhibitor. This protease inhibitor is no longer used because it is toxic. To minimize degradation of the proteins in the complex the water extract is maintained on ice to minimize proteolytic degradation.

The present method includes the steps of collecting bacterial cells, extracting the cells in sterile water, separating and discarding membrane fragments from the water extract resulting in a solution containing the Invaplex, and isolating the Invaplex from the solution. Growing gram-negative bacteria in culture is known to a person with ordinary skill in the art. For a general reference, please see *Manual of Methods for General Bacteriology,* 1981, Washington, D.C., P. Gephardt et al., eds. Media and conditions for growth are discussed for *Shigella* in detail in Materials and Methods below. After growth, the bacterial cells are extracted in sterile water, 20 mM Tris-HCl, normal saline (0.15M NaCl), or other buffers as long as the conditions allow binding of the Invaplex 24 and Invaplex 50 fractions to the desired column.

It is preferable to delete detergents in the extraction solution since detergents tend to form mixed micelles (micelles containing a variety of proteins) which may not behave in a consistent manner on the ion-exchange column. Detergents will also solubilize integral membrane proteins which may interfere with the Invaplex product. Finally, detergents may disrupt or denature the Invaplex and solubilize all of the indivdual components of the complex. Sterile water can be prepared by methods known in the art, for example, filtering through a 0.10, 0.22 or 0.45 micron filters. The concentration of bacterial cells to water is preferably $1\times10^7$ to about $2\times10^{12}$ cells per ml of water or buffer, more preferably between $1\times10^8$ to about $2\times10^{11}$.

Extraction time is preferably regulated since if it is too long degradation of product may result, and too short will result in poor yield of product.

A protease inhibitor can be added, during the extraction step to aid in reducing the protein degradation of the final product. Examples of protease inhibitors which could be added include phenylmethylsulfonyl fluoride (PMSF). Other protease inhibitors are available such as serine protease inhibitors but they are usually somewhat toxic. If the invaplex is to be administered to living cells, it would be preferable to delete the protease inhibitors or remove it from solution prior to administration due to the toxicity of the protease inhibitors. However, if the Invaplex is to be used for an ELISA reagent, the protease inhibitor could be left in the solution, in fact it would be preferable to have it in the solution.

Next, the cells and membrane fragments are removed from the solution by methods known in the art such as centrifugation, filtration, microfiltration, ultrafiltration, however, ultracentrifugation is preferable for removing the small membrane fragments before the solution is subjected to ion-exchange chromatography. Following extraction, the complex may be separated from the cellular debris by any technique suitable for separation of particles in complex mixtures. The complex may then be purified by anion or cation exchange chromatography or other isolation techniques which may include, but are not limited to, ammonium sulfate or ethanol precipitation, acid extraction, electrophoresis, isoelectric focusing, immunoadsorption, phosphocellulose chromatography, hydrophobic interaction chromatography, affinity chromatography, immunoaffinity chromatography, size exclusion chromatography, liquid chromatography (LC), high performance LC (HPLC), fast performance LC (FPLC), hydroxylapatite chromatography and lectin chromatography. Anion exchangers include diethylaminoethyl (DEAE) {—OCH2CH2N+H(CH2CH3)

2}; quaternary aminoethyl (QAE) {—OCH2CH2N+(C2H5)—CH2CHOH—CH3}; and quaternary ammonium (Q) {—OCH2CHOH—CH3CHOH—CH2N+(CH3)C3}. Such functional groups are bound to various supports, each support varying in particle size, but also vary with respect to the support material. Examples of support material include: Monobeads, 10 um bead of hydrophilic polystyrene/divinylbenzene {i.e., Mono Q (Pharmacia, Upsula, Sweden)}, Minibeads, 3 um bead of a hydrophilic polymer {i.e., Mini Q (Pharmacia)}, 15 & 30 um monodispersed hydrophilized rigid, polystyrene/divinylbenzene beads {i.e., Q (Pharmacia)} Sepharose, 34–50 um highly crosslinked agarose beads {i.e., HiTrap Q (Pharmacia) and Econo-Pac High Q (Bio-Rad)} Sepharose Fast Flow, 90 um agarose beads {i.e., QSepharose Fast Flow (Pharmacia)}, Sepharose Big Beads, 100–300 um agarose beads {i.e., QSepharose Big Beads (Pharmacia)}.

The chloride ion (Cl—) is the counterion of choice for anion exchange chromatography, with the choice of buffer dependent on the required pH interval. While Tris has a an effective buffering range of 7.6 to 8.0. Other buffers which may be used include: N-methyl-diethanolamine (pH 8.0–8.5), diethanolamine (pH 8.4–8.8), 1,3-diamino-propane (pH 8.5–9.0), ethanolamine (pH 9.0–9.5), and potentially piperazine (pH 9.5–9.8). These buffers are used at a low concentration, usually 20 mM, but could be as high as 50 mM.

Other columns or methods may be used as long as they maintain native structure of the Invaplex so that immunogenicity and function is intact, allow large volumes of a dilute protein solution to be loaded and concentrated, the buffers are biologically compatible, the method is rapid in order to minimize degradation of product and few processing steps are required.

It is preferable that each column be dedicated to a specific serotype and strain of *Shigella*. The optimal protein concentration in the final product would be approximately 10 doses per ml. But the range could be as low as 0.1 dose per ml (protein conc. of 2.5 ug/ml) up to much higher levels of 5000 doses per ml (protein conc. of 125 mg/ml) as long as solubility is maintained, i.e. concentration not too high to cause precipitation and not too low to make filtration too costly and time consuming.

Ideally we are achieving 0.25 mg/ml to 5 mg/ml in peak fractions of Invaplex 24 and Invaplex 50. If protein concentration is less than 0.25 mg/ml than it must be concentrated by centrifugal or tangential flow size-exclusion filtration (mw cutoff of 10000 to 100,000 more preferably 30,000 mw cutoff).

Using the method described in the Materials and Methods below, the fractions containing the greatest amount of IpaB and IpaC were found in fractions eluted at 24% buffer and 50% buffer from the ion-exchange column, resulting in Invaplex 24, and Invaplex 50.

This method needs to be modified minimally for use with other gram-negative bacteria. For example, other ion-exchange columns can be used, and different antibodies must be used to probe for the target antigens. For example, antibodies for SipB and SipC would have to be used to identify peak fractions containing the complex obtained from *Salmonella* spp. *Yersinia* would need anti YOP protein antibodies (Corneliz and Wolf-Watz, 1997, *Mol. Microbiol.* 23, 861–867).

Other methods for producing Invaplex include methods whereby individual invasin proteins are combined with LPS in order to form a complex with a native configuration. In addition, the invasins/LPS complex can be further purified from other components in the Invaplex 24 and Invaplex 50 fractions by purification techniques as desribed above and below.

In one embodiment, the present invention relates to a vaccine for heterologous protection against gram-negative bacteria. The vaccine comprises Invaplex 50 from a gram-negative bacteria comprising in a native configuration LPS, IpaB, IpaC, IpaD, VirG, 72 kDa component of Invaplex 50, and 84 kDa component of Invaplex 50. The vaccine can be used to immunize subjects for protection against infection with a gram negative bacteria heterologous, or different, than the gram negative bacteria from which the Invaplex vaccine was isolated. The vaccine can be prepared by isolating Invaplex 50 using methods described in detail above or below or by isolating recombinant proteins and combining them to form an Invaplex 50-like composition. One or more isolated Invaplex is prepared for administration to mammals by methods known in the art, which can include filtering to sterilize the solution, diluting the solution, adding an adjuvant and stabilizing the solution. One particular advantage of the present invention is that Invaplex preparations do not need to be administered with an immunopotentiator such as an adjuvant or a carrier, since the Invaplex itself functions as such. This characteristic as such does not preclude the use of immunopotentiators in compositions of the present invention. As such, in one embodiment, a composition of the present invention can include one or more Invaplexes and one or more adjuvants or carriers.

Adjuvants are typically substances that generally enhance the immune response of an animal to a specific antigen. Suitable adjuvants include, but are not limited to, Freund's adjuvant, other bacterial cell wall components, aluminum-based salts, calcium-based salts, silica, polynucleotides, toxoids, serum proteins, viral coat proteins, other bacterial-derived preparations, gamma interferon, block copolymer adjuvants, such as Hunter's Titermax adjuvant (CytRx™, Inc. Norcross, Ga.), Ribi adjuvants (availabe from Ribi ImmunoChem Research, Inc. Hamilton, Mo.), and saponins and their derivatives, such as Quil A (available from Superfos Biosector A/S, Denmark).

Carriers are typically compounds that increase the half-life of a therapeutic composition in the treated animal. Suitable carriers include, but are not limited to, polymeric controlled release formulations, biodegradable implants, liposomes, oils, esters, and glycols.

The vaccine can be lyophilized to produce a vaccine against gram-negative bacteria in a dried form for ease in transportation and storage. The dried compositions can be used for oral delivery. Invaplexes can also be mixed with a pharmaceutically acceptable excipient, such as an isotonic buffer that is tolerated by the organism to be administered the vaccine. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer, and Tris buffer, while examples of preservatives include thimerosal, m- or 0-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

Further, the vaccine may be prepared in the form of a mixed vaccine which contains the one or more Invaplexes described above and at least one other antigen as long as the added antigen does not interfere with the effectiveness of the vaccine and the side effects and adverse reactions are not increased additively or synergistically. The vaccine can be associated with chemical moieties which may improve the vaccine's solubility, absorption, biological half life, etc. The moieties may alternatively decrease the toxicity of the vaccine, eliminate or attenuate any undesirable side effect of the vaccine, etc. Moieties capable of mediating such effects are disclosed in *Remington's Pharmaceutical Sciences* (1980). Procedures for coupling such moeities to a molecule are well known in the art.

The vaccine may be stored in a sealed vial, ampule or the like. The present vaccine can generally be administered in the form of a spray for intranasal administration, or by nose drops, inhalants, swabs on tonsils, or a capsule, liquid, suspension or elixirs for oral administration. In the case where the vaccine is in a dried form, the vaccine is dissolved or suspended in sterilized distilled or deionized water before administration.

Generally, the vaccine may be administered to a subject orally, subcutaneously, intradermally, transdermally, or intramuscularly but preferably intranasally or orally, rectally and vaginally in a dose effective for the production of neutralizing antibody and resulting in protection from infection or disease. Mucosal vaccination using the composition of the present invention is expected to be an effective route of vaccination because it will induce secretory antibodies at the mucosal surface in addition to inducing bactericidal antibodies in the serum.

By subject is meant an animal, bird, fish and mammal including humans. The vaccine may be in the form of single dose preparations or in multi-dose flasks which can be used for mass vaccination programs. Reference is made to *Remington's Pharmaceutical Sciences*, Mack Publising Co., Easton, Pa., Osol (ed.) (1980); and *New Trends and Developments in Vaccines*, Voller et al. (eds.), University Park Press, Baltimore, Md. (1978), for methods of preparing and using vaccines. Acceptable protocols to administer compositions in an effective manner include individual dose size, number of doses, frequencey of dose administration, and mode of administration. Determination of such protocols can be accomplished by those skilled in the art. A preferred single dose of an Invaplex composition is from about 0.1 ug/kg body weight to about 100 ug/kg body weight. Boosters are preferably administered when the immune response of an organism is no longer being effectively modulated. Such compositions can be administered from about two weeks to several years after the original administration. A preferred administration schedule is one in which from about 0.5 ug to about 10 ug of a composition per kg body weight of the organism is adminsitered from about one to about four times over a time period of from about one month to about 6 months.

In another embodiment, the present invention relates to a method of reducing gram-negative infection symptoms in a patient by administering to said patient an effective amount of Invaplex antibodies, including those made in humans, either polyclonal or combinations of monoclonals to Invaplex, as described above. When providing a patient with Invaplex antibodies, the dosage administered will vary depending upon such factors as the patient's age, weight, height, sex, general medical condition, previous medical history, etc. In general, it is desirable to provide the recipient with a dosage of the above compounds which is in the range of from about 1 pg/kg to 500 mg/kg (body weight of patient), although a lower or higher dosage may be administered.

The present invention also provides a kit comprising a pharmaceutical (for prophylaxis i.e. a vaccine or for therapy i.e. a therapeutic) as described above in a container preferably a pre-filled syringe or glass vial/ampoule with printed instructions on or accompanying the container concerning the administration of the pharmaceutical to a patient to prevent or treat conditions caused by gram-negative bacterial infections.

Described below are examples of the present invention which are provided only for illustrative purposes, and not to limit the scope of the present invention. Other suitable modifications and adaptations of the variety of conditions and parameters normally encountered in this art which are obvious to those skilled in the art are within the spirit and scope of the present invention.

The following methods and materials were used in the examples below.

Materials and Methods

Bacterial Growth and Strains. *Shigella* strains used in these studies are part of the WRAIR collection. They include *Shigella flexneri* 2a (2457T), *S. sonnei* (Mosley), and *S. boydii* 2, *Shigella flexneri* 5 (M90T-W, Vir+), *S. flexneri* 5 (M90T-55, Vir−), *S. flexneri* 2a (M42-43a, Vir−), *S. dysenteriae* 1 (Ubon), and enteroinvasive *E. coli* Q152. Isolated red *Shigella* colonies grown on Congo Red TSA plates were used to inoculate 50 ml of PenAssay (Antibiotic Medium #3, Difco Laboratories, Detroit, Mich.) broth at 37° C. After 4 hrs of growth, 10 ml of the log phase culture were added to each liter of pre-warmed (37° C.) PenAssay broth. The 1 liter cultures were incubated overnight at 37° C. in a shaking incubator.

Water Extraction of *Shigella* proteins A modification of the original water extraction procedure described by Oaks et al. was used to prepare the material from which the *Shigella* invasin complex was isolated. Typically, four liters of an overnight culture of virulent shigellae were used for one batch of water extract. The bacterial cells were collected by centrifugation, suspended in sterile, deionized water (0.45 um membrane filtered) at a volume of 50 ml per liter of overnight culture, and then incubated at 37° C. in a shaking water bath (apx 200 rpm) for 2 hr. After extraction with water, the cells were collected by centrifugation at 16000×g for 30 min at 4° C. The supernatant was collected and centrifuged at 100,000×g for 1 hr at 4° C. to pellet membrane fragments. All 100,000×g supernatants for a single batch of water extract were pooled and stored at −70° C. The water extract was maintained on ice when possible and protease inhibitors were not used during the procedure.

Characterization of Water Extract. The total protein content of each batch of water extract was measured by the bicichoninic acid assay (Pierce Chemical Co., Rockford, Ill.). Water extract was analyzed for the presence of IpaB and IpaC by western blots or spot blots using monoclonal antibodies specific for IpaB (mab 2F1, Mills et al., 1988, Infect. Immun. 56, 2933) and IpaC (mab 2G2, Mills et al, 1988, supra). Only water extracts that were positive for these Ipa proteins were used for invasin complex purification.

FPLC (Fast Protein Liquid Chromatography). Ion exchange chromatography was used to isolate invasin complex fractions from water extract. Either a 5 ml anion exchange HiTrap™Q or 50 ml HiLoad™ 26/10 Q Sepharose High Performance (Amersham-Pharmacia Biotech, Inc., Piscataway, N.J.) column was equilibrated with 20 mM Tris-HCl, (Sigma Chemical Co., St. Louis, Mo.), pH 9.0 (buffer A) at ambient temperature. Prior to loading, Tris-HCl (0.2M, pH 9.0) was added to the water extract sample to a final concentration of 20 mM, after which 20 to 900 mls (approximately 8 to 300 mg total protein) of the water extract was loaded onto the column at a flow rate of 2 mls/min for the 5 ml column and 6 mls/min for the 50 ml column. After loading, the column was washed with at least 6 column volumes of buffer A. All elutions were carried out with step gradients of 24% buffer B, followed by a 50% buffer B step, and finally the column was washed with 100% buffer B (1M NaCl in 20 mM Tris-HCl, pH 9.0). Protein passing through the column was monitored at 280 nm and recorded via the PowerChrom data acquisition and analysis software (ADInstruments, Mountain View, Calif.) for the Macintosh computer operating system. Two to 2.5 ml fractions were collected in polypropylene tubes and immediately placed at ~70° C. Buffer steps were changed after the optical density at 280 nm (OD280) returned to baseline for the previous buffer step. The buffer B diluent was 20 mM Tris-HCl, pH 9.0. After washing with 100% buffer B, the column was reequilibrated with buffer A before the next run. Each column used in these studies was dedicated to a specific serotype and strain of Shigella.

Each fraction was analyzed by spot blot for the presence of IpaC and IpaB. Fractions (usually 1 or 2) containing the greatest amount of IpaB and IpaC in 24% buffer B were pooled as were peak Ipa protein fractions in 50% buffer B, resulting in Invaplex 24 and Invaplex 50, respectively, for a run. Invaplex 24 and Invaplex 50 run pools, once determined to be relatively similar with respect to IpaB, IpaC, and IpaD content (determined by western blot), LPS content (determined by silver stain analysis of gels, see below) and total protein composition, were combined, identified as a particular "lot" of Invaplex 24 or Invaplex 50, and stored at −80° C.

Water Extract and LPS ELISAs. Antigens used in ELISAs include water extracts from vir+ (M90T-W) and vir− (M90T-55) strains of S. flexneri 5 and also purified LPS from either S. flexneri 2a or S. sonnei. Antigen was diluted in carbonate coating buffer (0.2 M carbonate, pH 9.8) and was added to polystyrene 96-well antigen plates (Dynex Technologies, Inc., Chantilly, Va.) at a concentration of 1 ug/well. Primary antibody was diluted in casein (2% casein in a Tris-saline buffer, pH 7.5) and incubated with the antigen-coated plates for 2 hrs. After 4 washes in PBS (10.75 mM sodium phosphate, 145 mM NaCl) with 0.05% Tween 20, plates were probed with commercial anti-guinea pig IgG, anti mouse IgG, or anti-mouse IgA conjugated with alkaline phosphatase (Kirkgard & Perry, Gaithersburg, Md.). The ELISA substrate was para nitrophenyl phosphate (1 mg/ml in 10% diethanolamine buffer, pH 9.8, containing 0.1 mg/ml $MgCl_2$ and 0.02% sodium azide). The O.D. was measured at 405 nm on a Molecular Devices (Menlo Park, Calif.) ELISA plate reader.

Affinity purification of antibodies to surface-exposed proteins. Nitrocellulose disks were placed on the surface of tryptic soy agar (TSA) plates and allowed to adhere to the agar surface. One colony of virulent S. flexneri 5 (M90T-W), suspended in 1.0 ml of 0.9% saline, was swabbed across the nitrocellulose membrane surface to provide abundant, isolated colonies after growth overnight at 37° C. After rinsing the disks with 10 mM Tris-HCl, 0.9% saline (Tris-saline), they were blocked with 2% casein solution containing sodium azide for at least 30 mins. Convalescent guinea pig serum from animals immunized with Invaplex 50 from S. sonnei Mosley and challenged intraoccularly with $3 \times 10^8$ S. sonnei 53G was diluted 1:300 in 2% casein filler and incubated with a nitrocellulose disk for 4 hours at room temperature. Each nitrocellulose disk was then washed extensively followed by antibody elution with a minimal amount of 0.2 M glycine, pH 2.8 for 30 mins. Eluted antibody was collected and neutralized to pH 7.4 with Tris base. Affinity-purified antibodies were used at a 1:3 dilution in 2% casein filler to probe Western blots.

Figure 13A:
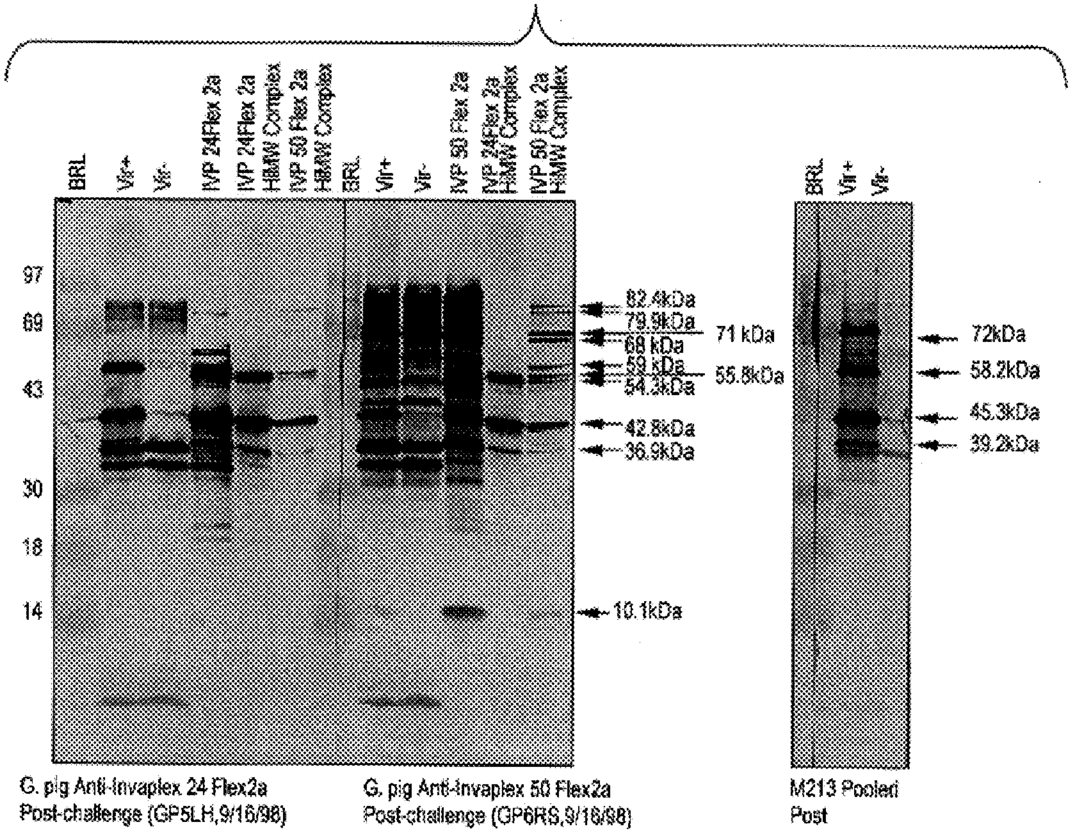
FIG. 13. Western blots. Antisera used in western blots included monoclonal antibodies to IpaB (2F1), IpaC (2G2) and IpaD (16F8) and a monkey convalescent serum pool (M213) which contains antibodies to all Ipa proteins (IpaA, IpaB, IpaC and IpaD) and VirG. Guinea pig sera used for western blots were from animals immunized with Invaplex 24 or Invaplex 50.
Figure 13B:
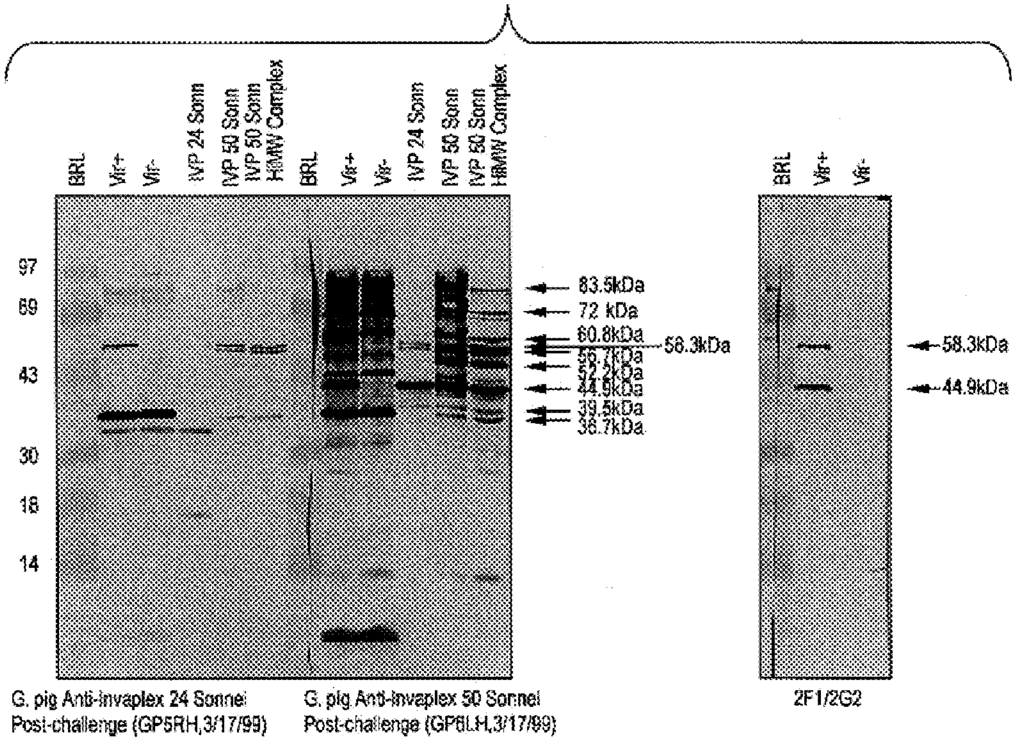

Electrophoresis and western Blots. Western blots were performed as previously described. Antisera used in western blots included monoclonal antibodies to IpaB (2F1), IpaC (2G2) and IpaD (16F8, Turbyfill et al., 1988, supra) and a monkey convalescent serum pool (M213) which contains antibodies to all Ipa proteins (IpaA, IpaB, IpaC and IpaD) and VirG. Guinea pig sera used for western blots were from animals immunized with Invaplex 24 or Invaplex 50 (FIG. 13). These sera were collected on day 0 (pre-bleed) and day 42 (14 days post immunization). The sera was diluted 1/300 for the western blots.

Silver staining was used to stain LPS in samples treated with proteinase K (Gibco-BRL, Bethesda, Md.) prior to loading on gels.

Immunogenicity and protective capacity of Invaplex 24 and Invaplex 50. The ability of the Invaplex fractions to promote an immune response in Balb/cByJ mice was tested in groups of 10 to 15 mice. Each mouse was immunized intranasally with 5 ug of Invaplex 24 or Invaplex 50 from S. flexneri 2a or S. sonnei on days 0, 14, and 28. Bivalent vaccines were constructed by combining equal amounts of S. flexneri 2a Invaplex 24 and S. sonnei Invaplex 50 (5 ug each per dose). Saline was used to immunize control animals. A total antigen volume of 25 ul was delivered in 5 to 6 small drops applied to the external nares with a micropipet. Blood was taken by tail bleed from all mice on days 0, 28, and 42.

Three weeks after the final immunization with either Invaplex 24 or Invaplex 50 from S. flexneri 2a or S. sonnei, mice (15 per group) were challenged intranasally with a lethal dose of S. flexneri 2a (2457T) ($1.0 \times 10^7$ cfu/30 ul) or S. sonnei ($8.0 \times 10^6$ cfu/30 ul) as described for the mouse lung model. Control mice, immunized with saline, were run for each challenge agent. Duplicate groups of animals were immunized with each monovalent vaccine, bivalent vaccine, or saline for parallel challenges with either S. flexneri 2a or S. sonnei.

The mouse challenge dose was prepared from a frozen lot of S. flexneri 2a or S. sonnei that had been harvested during the log phase of growth, which is the time of optimal invasiveness for shigellae, and then stored in liquid nitrogen (Oaks, unpublished data). Prior to intranasal immunization or challenge, mice were anesthetized with a mixture of ketamine hydrochloride (40 mg/kg) (Ketaset®, Fort Dodge Laboratories, Inc., Fort Dodge, Iowa) and xylazine (12 mg/kg) (Rompun®, Bayer Corp., Shawnee Mission, Kans.).

Statistical Analysis. Statistical computations were performed with the Statview program (SAS Institute Inc., Cary, N.C.). The Fisher exact test was used for protection experiments and the Wilcoxon signed rank test was used for analysis of serological data. Linear regression was used for analysis of dose-response experiment data.

EXAMPLE 1

Figure 15:
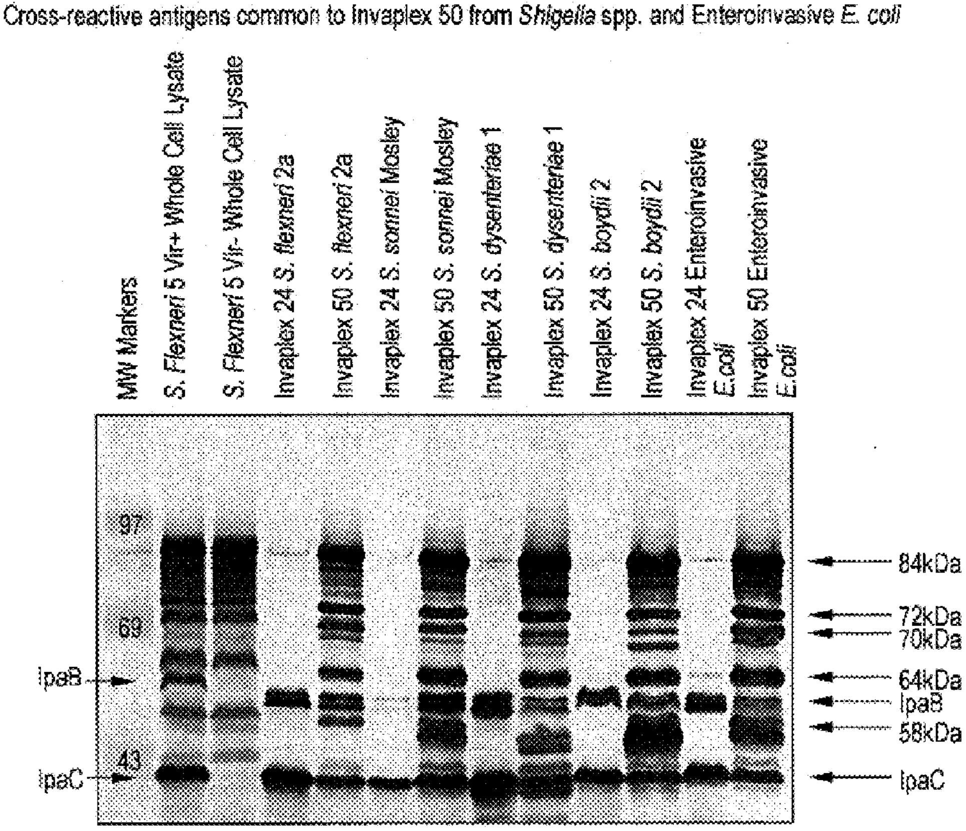
FIG. 15. Cross-reactive antigens common to Invaplex 50 from all *Shigella* spp and enteroinvasive *E. coli*. Immune serum from a guinea pig (GP 6LH) immunized with *S. sonnei* Invaplex 50 and subsequently challenged with *S. sonnei*, was used in this western blot to probe Invaplex 24 and Invaplex 50 preparations from *S. flexneri* 2a, *S. sonnei* (Mosley), *S. dysenteriae* 1, *S. boydii* 2 and enteroinvasive *E. coli* (lanes are labeled with antigen content). Each lane of this western blot was loaded with 15 μg of the indicated Invaplex. The GP 6LH antiserum contains antibodies to several *Shigella* proteins, including IpaB, IpaC, 84 kDa, 72 kDa, 70 kDa, 64 kDa, and 58 kDa proteins. Whole cell lysates of *S. flexneri* 5 Vir+ and *S. flexneri* 5 Vir− are in the left two lanes of the blot. The extreme left lane contains pre-stained molecular size standards (MW Markers). The proteins samples were initially separated on a 9% acrylamide gel prior to blotting. *Shigella* antigens are indicated with arrows on the right hand side of the blot.
Figure 16:
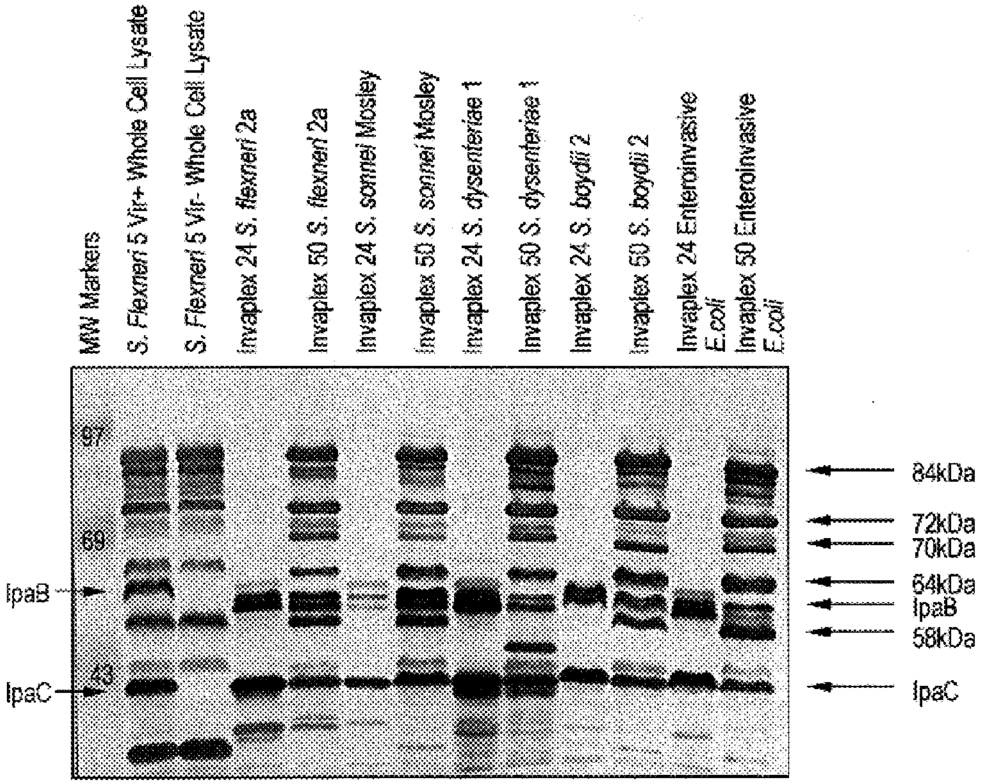
FIG. 16. Cross-reactive antigens common to Invaplex 50 from all *Shigella* spp and enteroinvasive *E. coli*. Immune serum from a guinea pig (GP 6RS) immunized with *S. flexneri* Invaplex 50 and subsequently challenged with *S. flexneri* 2a, was used in this western blot to probe Invaplex 24 and Invaplex 50 preparations from *S. flexneri* 2a, *S. sonnei* (Mosley), *S. dysenteriae* 1, *S. boydii* 2 and enteroinvasive *E. coli* (lanes are labeled with antigen content). Each lane of this western blot was loaded with 15 μg of the indicated Invaplex. The GP 6RS antiserum contains antibodies to several *Shigella* proteins, including IpaB, IpaC, 84 kDa, 72 kDa, 70 kDa, 64 kDa, and 58 kDa proteins. Whole cell lysates of *S. flexneri* 5 Vir+ and *S. flexneri* 5 Vir− are in the left two lanes of the blot. The extreme left lane contains pre-stained molecular size standards (MW Markers). The proteins samples were initially separated on a 9% acrylamide gel prior to blotting. *Shigella* antigens are indicated with arrows on the right hand side of the blot.

The *Shigella* Invaplex (invasin complex) is prepared by extracting intact virulent shigellae with water followed by anion-exchange chromatography of the water extract. Peaks eluted with step gradients of 0.24M NaCl and 0.5M NaCl contain IpaB, IpaC and LPS (Turbyfill, 2000, supra). These peaks are called Invaplex 24 and Invaplex 50. Both Invaplex peaks are protective in guinea pigs. Common components of the two forms of Invaplex include LPS, IpaB, IpaC and IpaD. However, Invaplex 50 contains additional antigenic proteins including VirG*, and the previously undescribed 72 kDa and 84 kDa polypeptides. Antibodies to the 72 kDa and 84 kDa polypeptides are produced in guinea pigs immunized with Invaplex 50 from *S. flexneri* or *S. sonnei* and these proteins are serological cross-reactive between all *Shigella* species and enteroinvasive *E. coli* (FIGS. 13, 15, 16). The 72 kDa and 84 kDa polypeptides are not virulence plasmid encoded.

Both forms of Invaplex have been isolated from all four species of *Shigella* and also from enteroinvasive *E. coli*. However with *S. sonnei* a few unique differences have been noted. Invaplex 24 from *S. sonnei* is deficient in the quantities of IpaB, IpaC and LPS as compared to Invaplex 24 isolated from other *Shigella* species. In contrast, *S. sonnei* Invaplex 50 is very similar, with respect to protein and LPS content, to the *S. flexneri* Invaplex 50. Invaplex 24 and 50 isolated from *S. boydii, S. dysenteriae* and enteroinvasive *E. coli* are similar to *S. flexneri* Invaplex. Further characterization of the Invaplex by size-exclusion chromatography, has identified a high molecular mass complex (HMMC, estimated size is between 1 and 2 million daltons) in *S. flexneri* Invaplex 24 that contains only IpaB, IpaC and LPS. A similar high molecular mass peak has been isolated from *S. flexneri* Invaplex 50, but in addition to IpaB, IpaC and LPS, it also contains the 72 kDa and 84 kDa polypeptides. Interestingly, the high molecular mass complex (HMMC or HiMW Complex in FIG. 13) is not found in *S. sonnei* Invaplex 24 but it is present in *S. sonnei* Invaplex 50 (FIG. 20). It remains to be determined if the HMMC is the functional antigenic component of the Invaplex product.

EXAMPLE 2

To date our studies have shown that Invaplex 24 and 50 from *Shigella flexneri* 2a are protective against homologous challenge in the mouse lethal lung model (Turbyfill & Oaks, 2000, supra; Oaks 1999, supra). *S. sonnei* Invaplex 50 also protects in mice but *S. sonnei* Invaplex 24 does not. Immunized animals (*S. flexneri* Invaplex 24 or 50, *S. sonnei* Invaplex 50) produce antibodies to LPS and the water extract which is a response very similar to that occurring after a natural infection in humans. Mice immunized with *S. sonnei* Invaplex 24, which is deficient in LPS, IpaB and IpaC, did not produce detectable antibodies to the Ipa proteins or LPS and were not protected from challenge. These results indicate that for the Invaplex vaccine to be protective it is necessary to have sufficient quantities of the invasins and LPS to produce a protective immune response.

Figure 2:
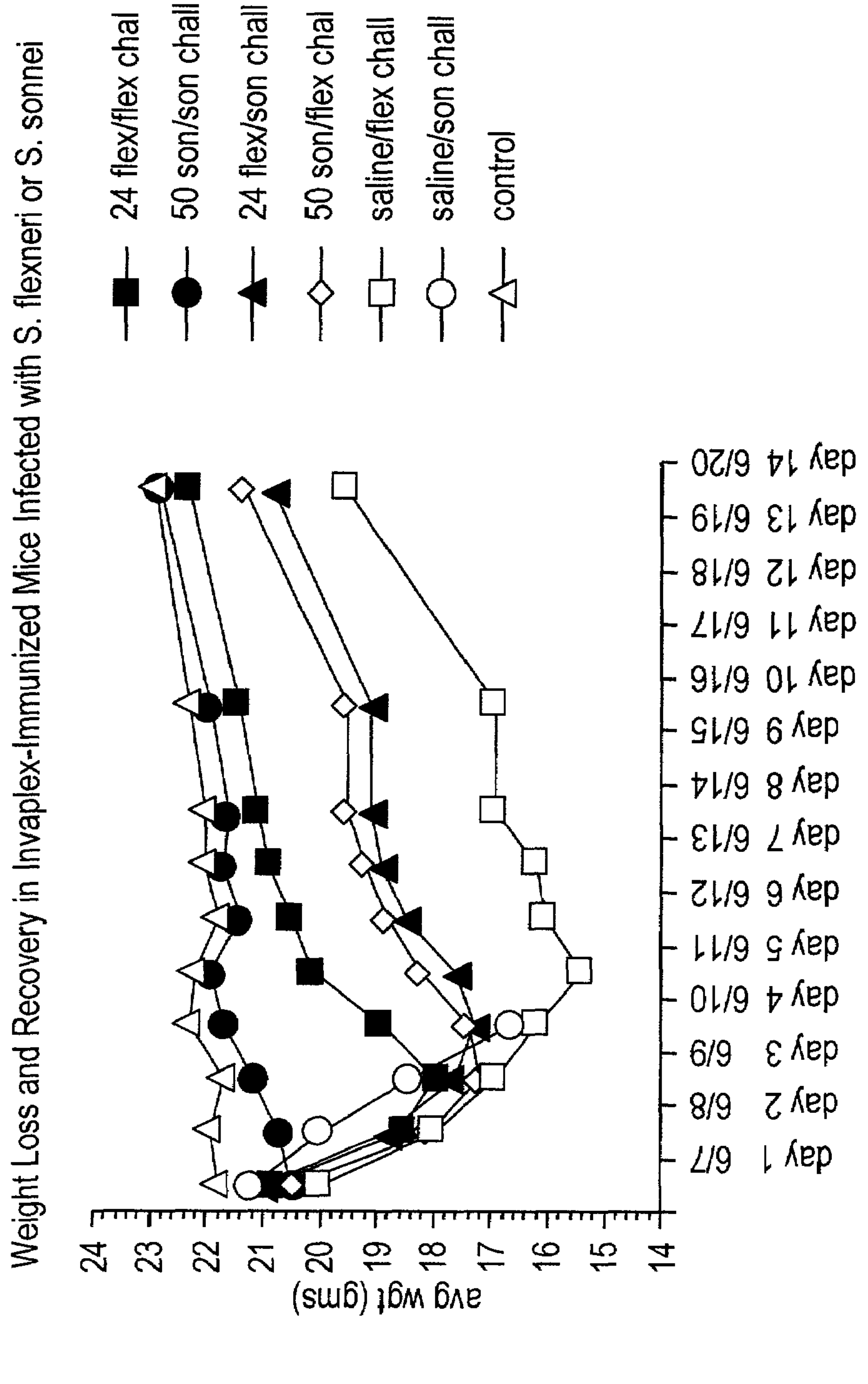
FIG. 2. Weight Loss and Recovery in Invaplex-Immunized Mice Infected with *S. flexneri* or *S. sonnei*. After infection with either *S. flexneri* 2a (flex chall) or *S. sonnei* (son chall) mice were weighed daily for 14 days. Groups used in this study include: *S. flexneri* Invaplex 24 (24 flex) immunized mice challenged with *S. flexneri* or *S. sonnei; S. sonnei* Invaplex 50 immunized (50 son) mice challenged with either *S. flexneri* or *S. sonnei*; mice immunized with saline and challenged with either agent, and untreated control mice.
Figure 3:
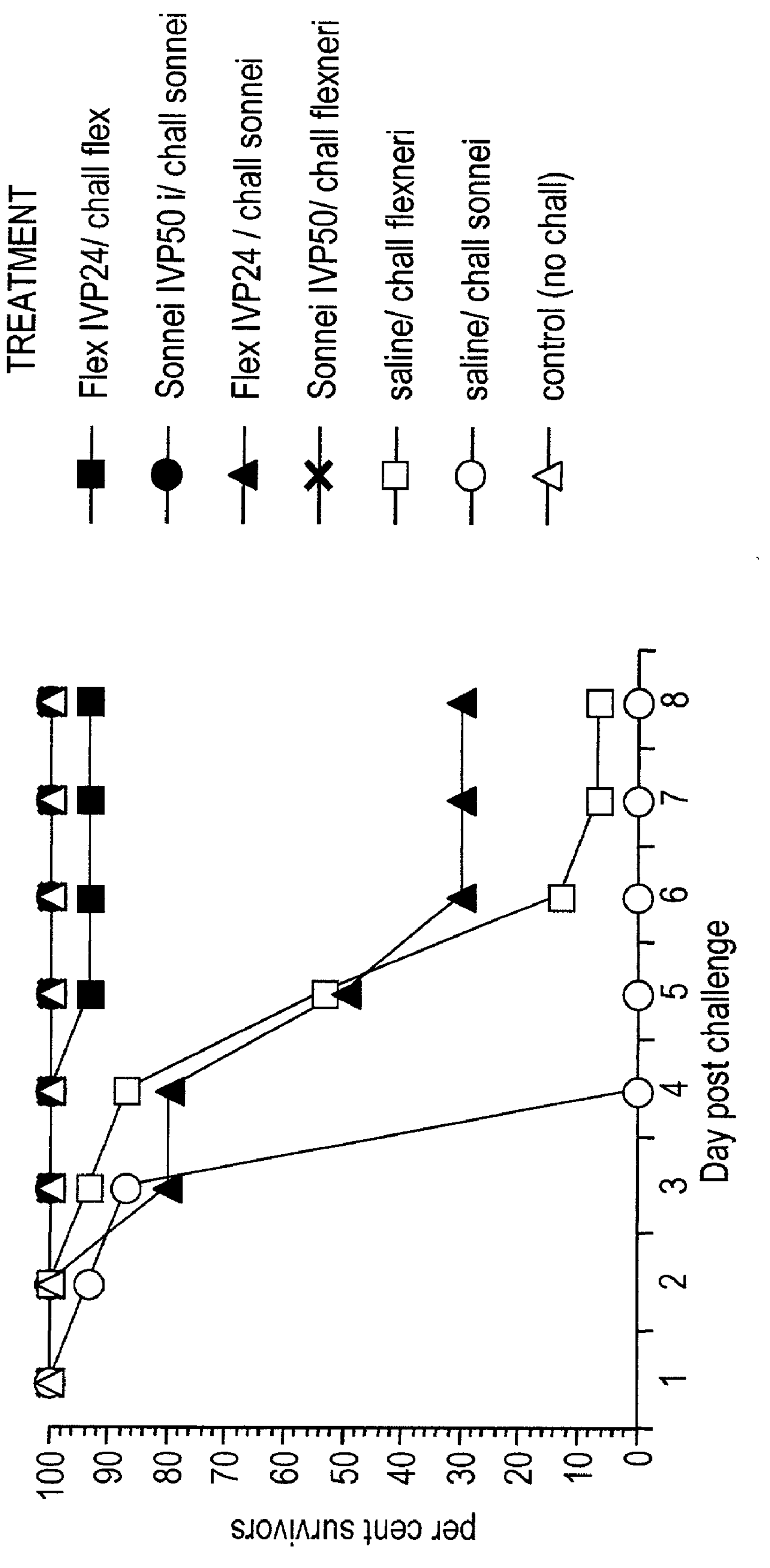
FIG. 3. Protective capacity of monovalent invaplex vaccines against homologous or heterologous challenges. After mice were infected with either *S. flexneri* 2a (chall flex ) or *S. sonnei* (chall sonnei) deaths were recorded daily for 14 days. Groups used in this study include: *S. flexneri* Invaplex 24 (24 flex) immunized mice challenged with *S. flexneri* or *S. sonnei; S. sonnei* Invaplex 50 immunized (50 son) mice challenged with either *S. flexneri* or *S. sonnei*; mice immunized with saline and challenged with either agent, and untreated control mice.
Figure 4:
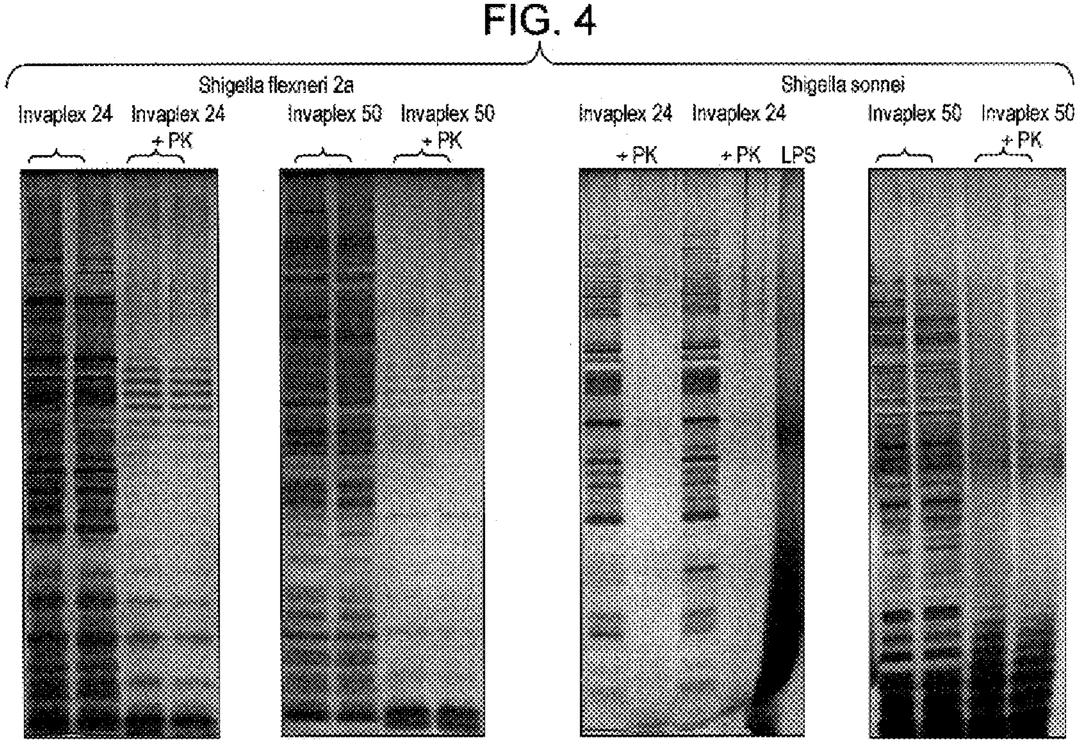
FIG. 4. Silver stained polyacrylamide gel showing Invaplex preparations treated with or without proteinase K (PK) to demonstrate the presence of lipopolysaccaride. Invaplex 24 and 50 preparations (2 preparations for each treatment) from *S. flexneri* 2a are on the left 2 panels; the two right-hand panels are from *S. sonnei.* LPS (see PK treated lanes) is stained and present in *S. flexneri* 2a Invaplex 24, *S. flexneri* 2a Invaplex 50, and *S. sonnei* Invaplex 50. LPS is not stained in significant quantities in *S. sonnei* Invaplex 24. Thus *S. sonnei* Invaplex 24 is deficient in LPS content relative to that found in Invapelx 24 or 50 from *S. flexneri.*
Figure 5:
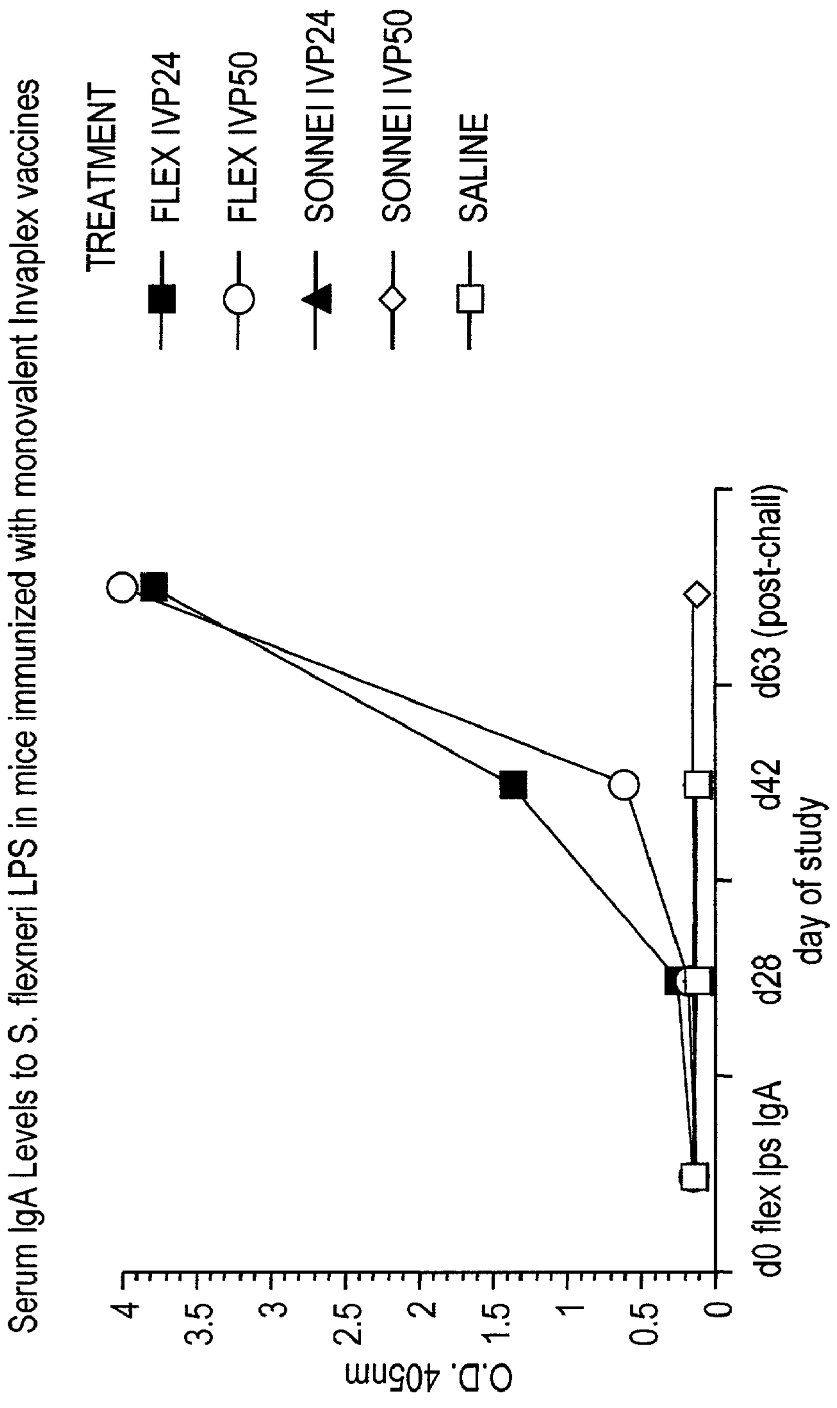
FIGS. 5–12. Antibody levels induced by immunization with either monovalent vaccine *S. flexneri* 2a Invaplex 24 or *S. sonnei* Invaplex 50. Antigens and antibody isotypes include: *S. flexneri* LPS (FIG. 5 for IgA, FIG. 6 for IgG); *S. sonnei* LPS (FIG. 7 for IgA, FIG. 8 for IgG); water extract/IgA levels (FIG. 9 for vir+ water extract, FIG. 10 for vir-water extract); and water extract/IgG levels (FIG. 11 for vir+ water extract, FIG. 12 for vir-water extract).
Figure 6:
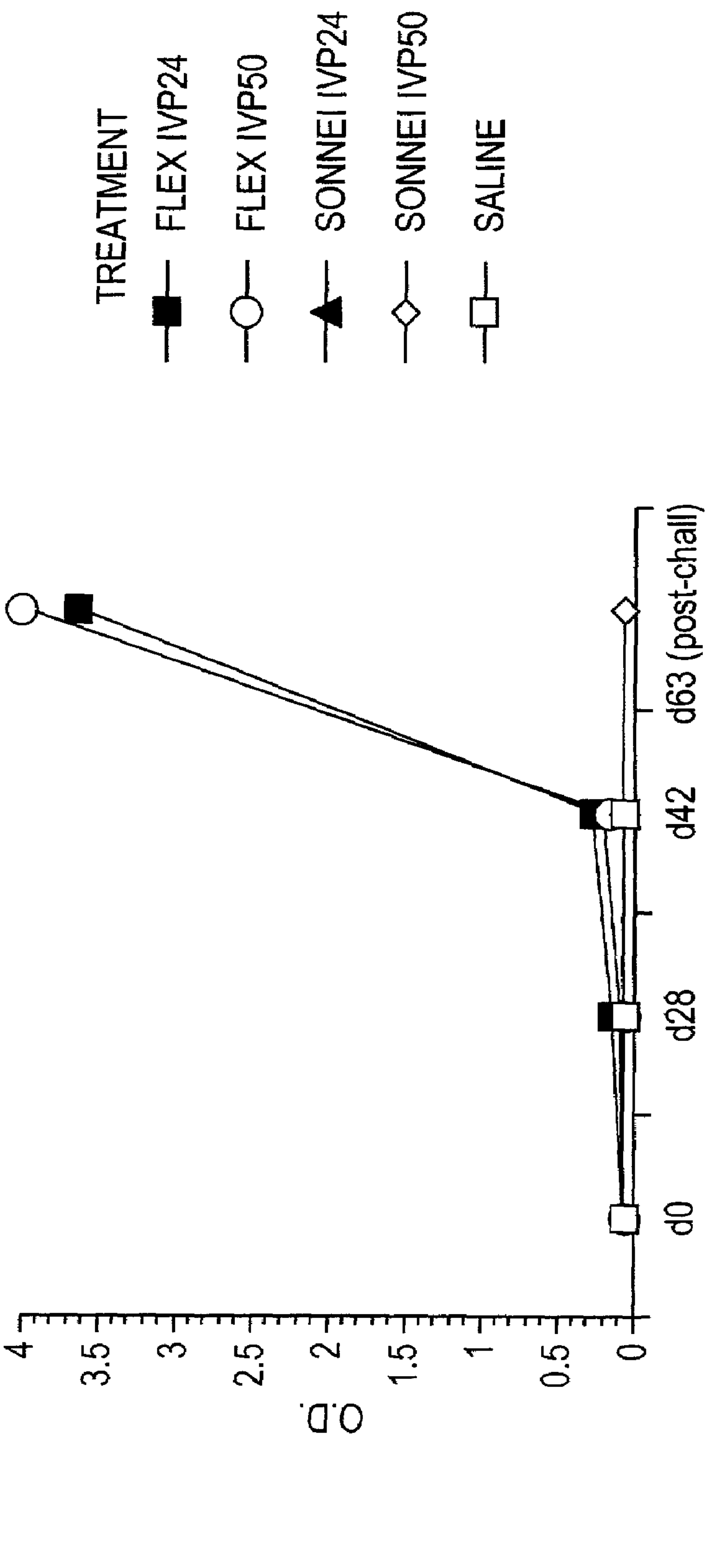
Figure 7:
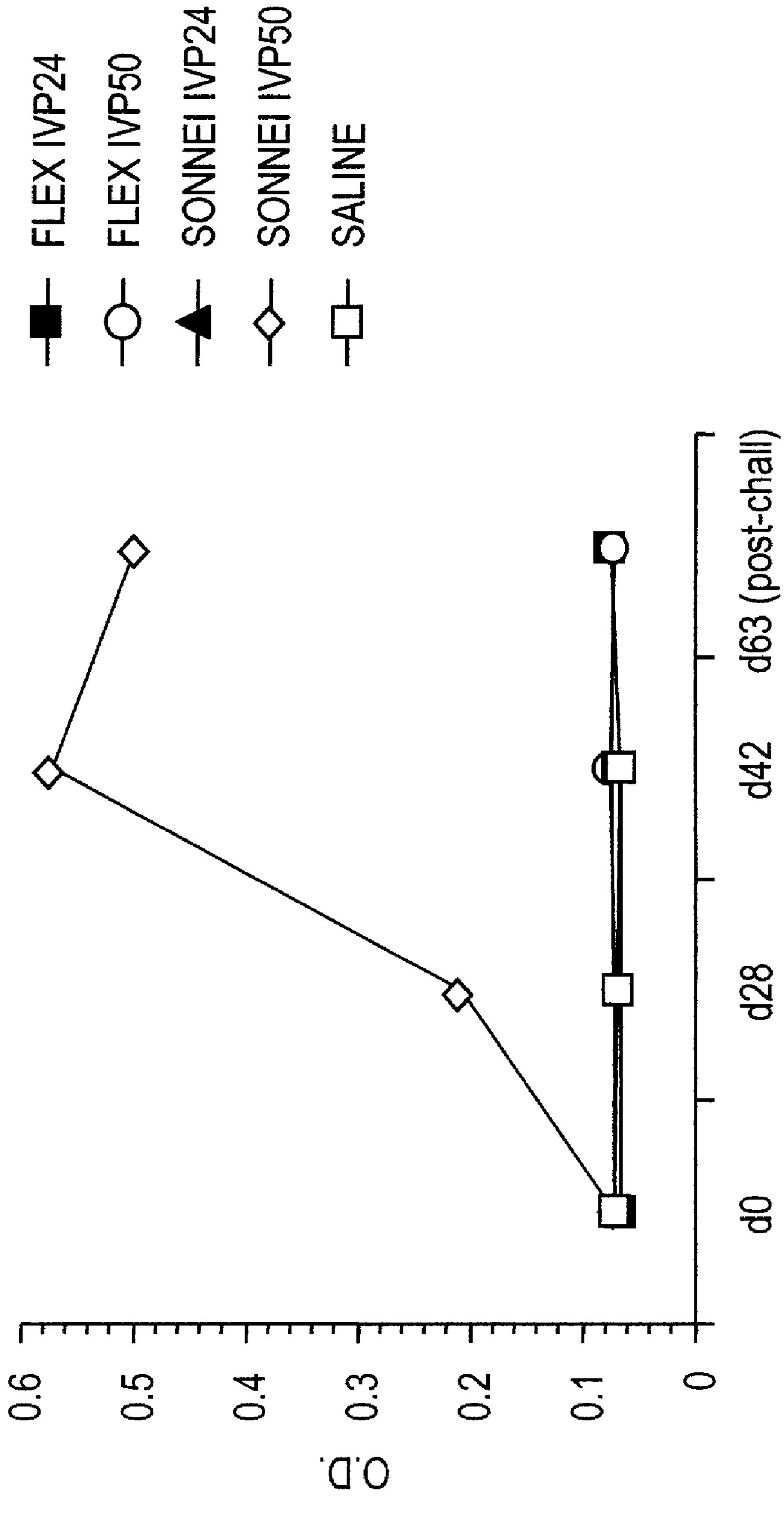
Figure 8:
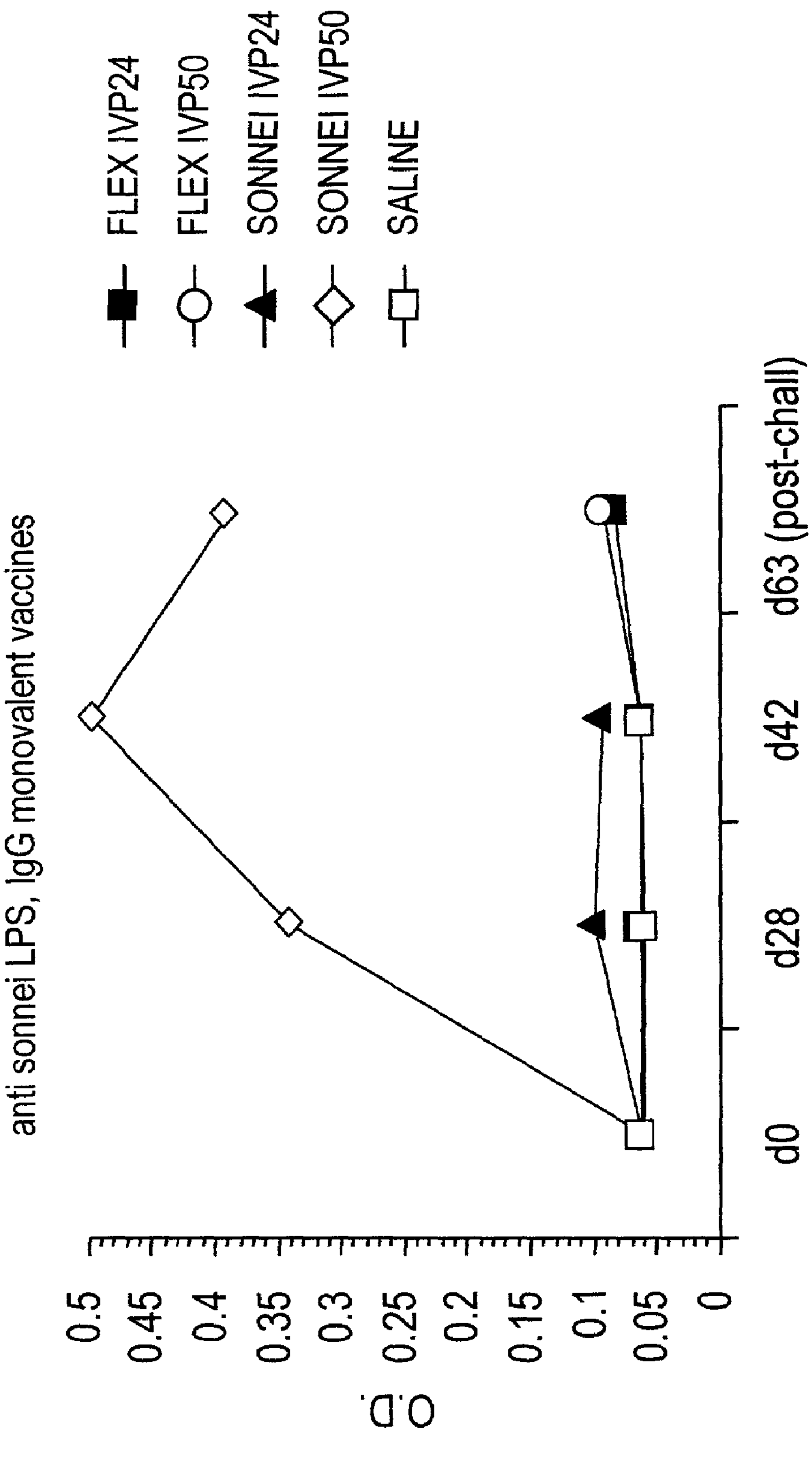
Figure 9:
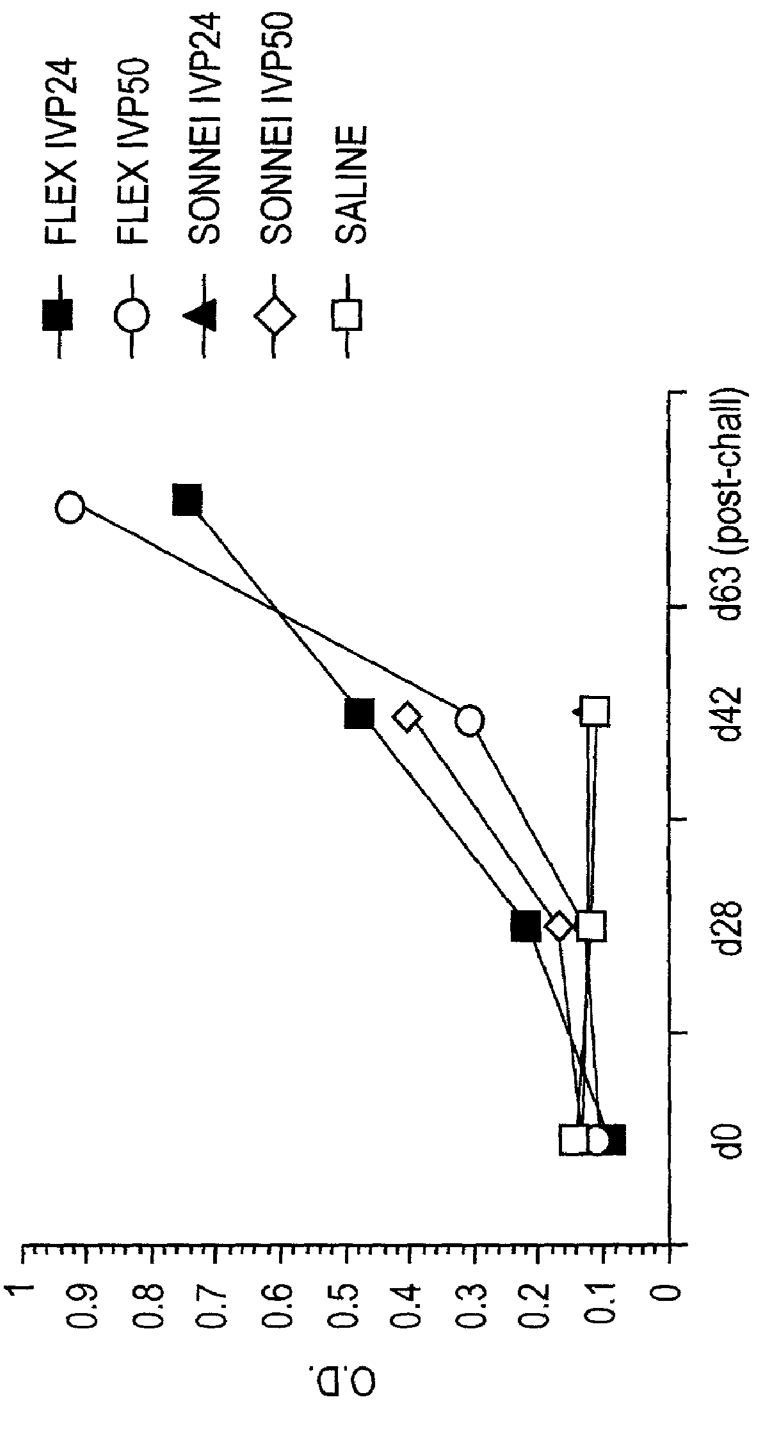
Figure 10:
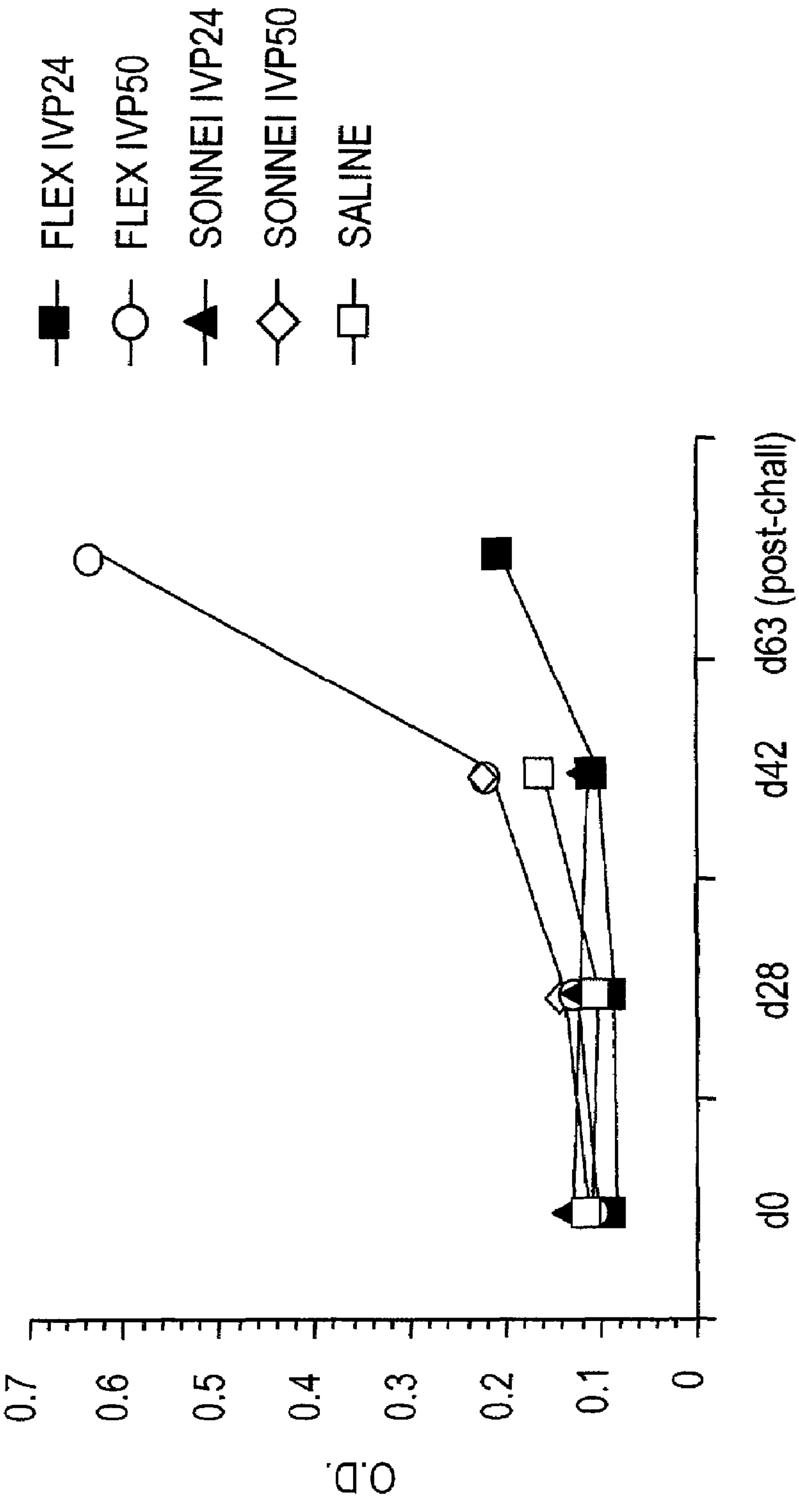
Figure 11:
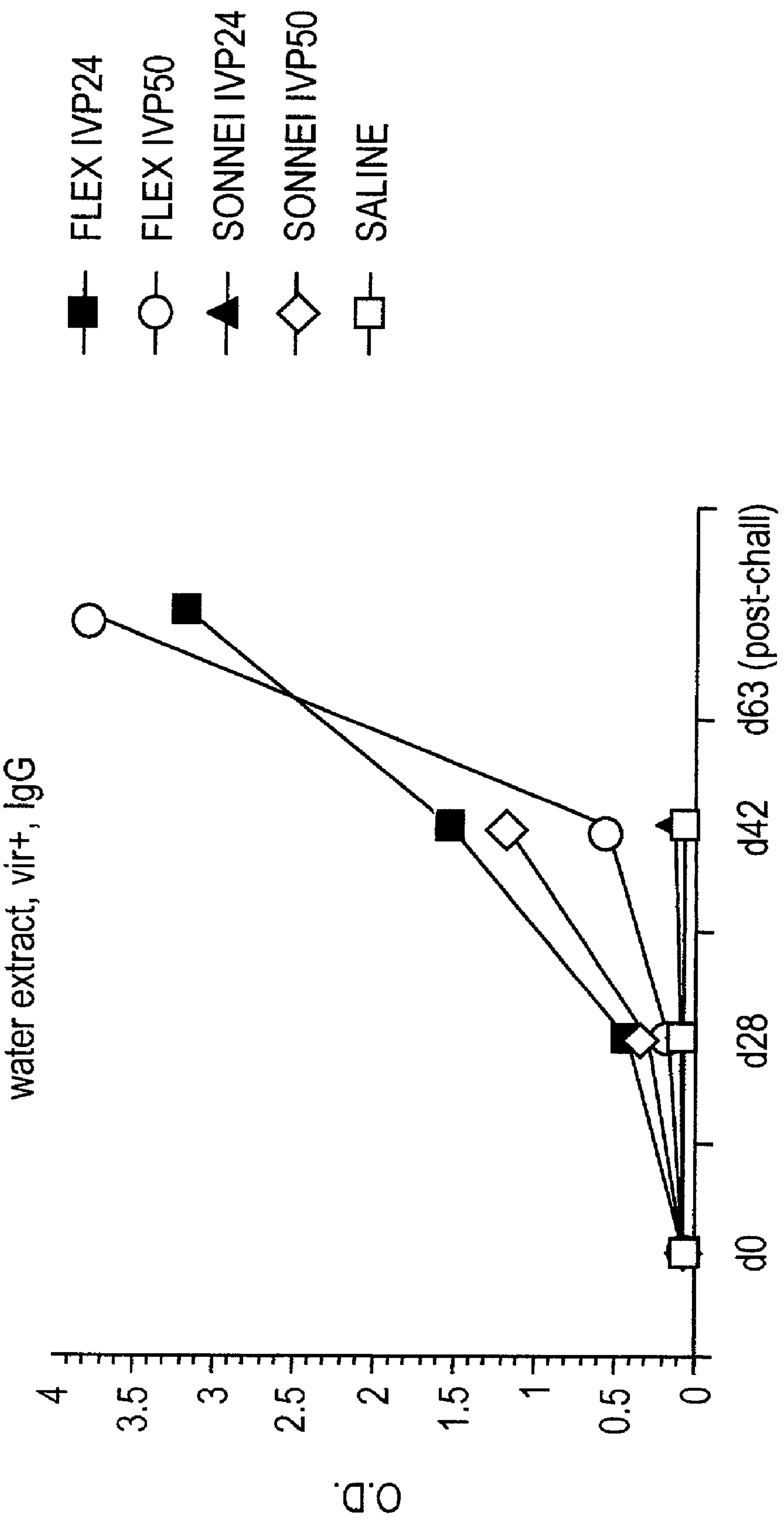
Figure 12:
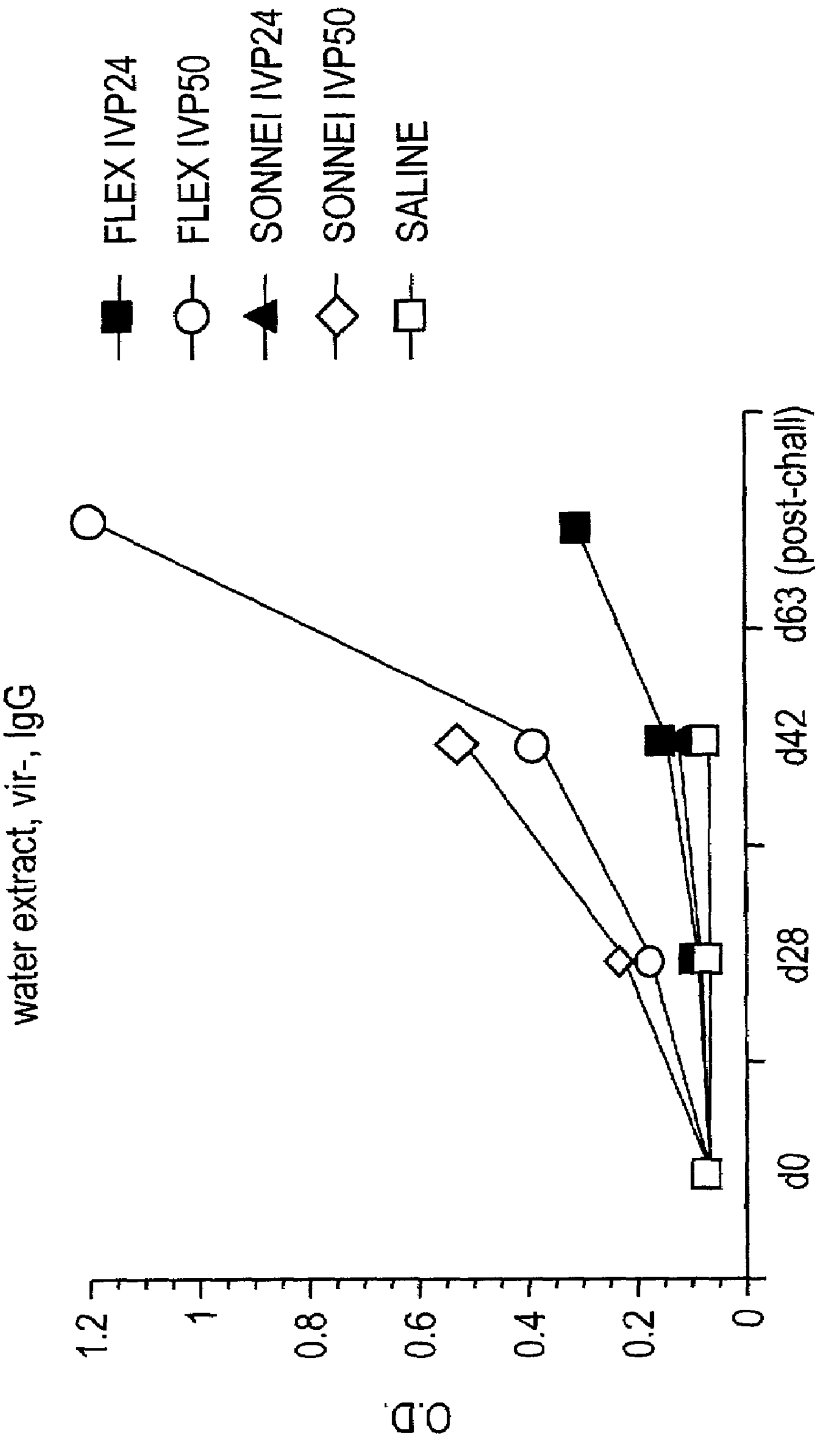

In other experiments, mice immunized with either the *S. flexneri* Invaplex 24 or *S. sonnei* Invaplex 50, were challenged with the heterologous agent. For example *S. flexneri* 24 immunized mice were challenged with *S. sonnei*. In these experiments only 30% of the *S. flexneri* Invaplex 24 immunized mice survived a lethal *S. sonnei* challenge (p=0.052). However, mice immunized with *S. sonnei* Invaplex 50 were protected against a lethal challenge of *S. flexneri* (89% survived, ($p<0.001$) (Table 1 and FIGS. 1-3). Weight loss and recovery results in FIG. 2 show that mice immunized with either *S. flexneri* Invaplex 24 or *S. sonnei* Invaplex 50 begin to recover after 1 to 3 days after infection with the homologous agent. Immunized mice challenged with the heterologous agent (for example, *S. sonnei* Invaplex 50 immunized mice challenged with *S. flexneri* 2a) also recovered after an initial weight loss.

These results indicate that protection against a heterologous species of *Shigella* (*S. flexneri* 2a) can be achieved with the *S. sonnei* Invaplex 50 vaccine. These results suggest that protective immunity stimulated by the Invaplex 50 vaccine may be directed at proteins common to both *S. flexneri* and *S. sonnei*. If so, similar protective immunity may be possible against *S. boydii* and *S. dysenteriae.*

Heterologous protection is not typically predicted for *Shigella* vaccines because LPS is considered to be the key target antigen for protective immunity and it is LPS which is the major antigenic difference between *Shigella* species. However the presence of conserved proteins, including IpaB and IpaC, which are present in all species of *Shigella*, may have played a crucial role in this cross-protective, heterologous immunity elicited by the *S. sonnei* Invaplex 50 vaccine. Furthermore, Invaplex 50 has a few additional antigens when compared to Invaplex 24. Specifically the 72 kDa and 84 kDa polypeptides are in Invaplex 50 and are immunogenic and cross-reactive between species. Evaluation of the immune response in the heterologous challenge studies described above (FIGS. 5-12) indicate that animals immunized with the *S. flexneri* Invaplex 24 developed a significant serum IgA and IgG immune responses to *S. flexneri* LPS and the water extract (vir+). Mice immunized with the *S. sonnei* Invaplex 50 vaccine produced IgA and IgG antibodies to *S. sonnei* LPS and also the water extract. Neither the *S. flexneri* nor the *S. sonnei* Invaplex vaccines stimulated production of antibodies to the heterologous LPS. Western blot analysis of *S. sonnei* Invaplex 50 immunized animals indicates that antibodies to IpaB and 84 kDa antigens were produced, whereas for *S. flexneri* 24 antibodies only to IpaB and IpaC were seen on western blots (FIG. 13).

TABLE 1

Protection Against a Lethal Heterologous *Shigella flexneri* 2a Challenge in Mice Immunized with *Shigella sonnei* Invaplex 50.

| Treatment | Challenge Agent | Survivors/Total | % Survivors | p value |
|---|---|---|---|---|
| | | Experiment 1 | | |
| *S. sonnei* Invaplex 50 | *S. sonnei* | 15/15 | 100 | <0.001 |
| Saline | *S. sonnei* | 0/15 | 0 | — |
| *S. sonnei* Invaplex 50 | *S. flexneri* 2a | 8/9 | 89 | <0.001 |
| Saline | *S. flexneri* 2a | 1/15 | 7 | — |

TABLE 1-continued

Protection Against a Lethal Heterologous *Shigella flexneri* 2a Challenge in Mice Immunized with *Shigella sonnei* Invaplex 50.

| Treatment | Challenge Agent | Survivors/Total | % Survivors | p value |
|---|---|---|---|---|
| | | Experiment 2 | | |
| *S. sonnei* Invaplex 50 | *S. sonnei* | 15/15 | 100 | <.001 |
| Saline | *S. sonnei* | 0/15 | 0 | — |
| *S. sonnei* Invaplex 50 | *S. flexneri* 2a | 15/15 | 100 | .006 |
| Saline | *S. flexneri* 2a | 8/15 | 53.3 | — |
| | | Experiment 3 | | |
| *S. sonnei* Invaplex 50 | *S. sonnei* | 15/15 | 100 | <.001 |
| Saline | *S. sonnei* | 0/15 | 0 | — |
| *S. sonnei* Invaplex 50 | *S. flexneri* 2a | 11/15 | 73.3 | .009 |
| Saline | *S. flexneri* 2a | 3/15 | 20 | — |

p-value was determined by the Fisher exact test.
Mice were immunized with 3 intranasal doses (5 ug/dose) of *S. sonnei* Invaplex 50, given at two-week intervals. Control mice were given saline. Three weeks after the final immunization, mice were given a lethal intranasal challenge of either *S. sonnei* or *S. flexneri* 2a. Deaths were recorded daily for 14 days.

Evaluation of the immune response in the heterologous challenge studies described above (FIGS. 5–12) indicate that animals immunized with the *S. flexneri* Invaplex 24 developed a significant serum IgA and IgG immune responses to *S. flexneri* LPS and the water extract (vir+). Mice immunized with the *S. sonnei* Invaplex 50 vaccine produced IgA and IgG antibodies to *S. sonnei* LPS and also the water extract. Neither the *S. flexneri* nor the *S. sonnei* Invaplex vaccines stimulated production of antibodies to the heterologous LPS. Western blot analysis of *S. sonnei* Invaplex 50 immunized animals indicates that antibodies to IpaB and 84 kDa antigens were produced, whereas for *S. flexneri* 24 antibodies only to IpaB and IpaC were seen on western blots (FIG. 13).

EXAMPLE 3

IgA Antibody Secreting Cells (ASC) in Guinea Pigs Immunized with *S. sonnei* Invaplex 50.

Figure 14:
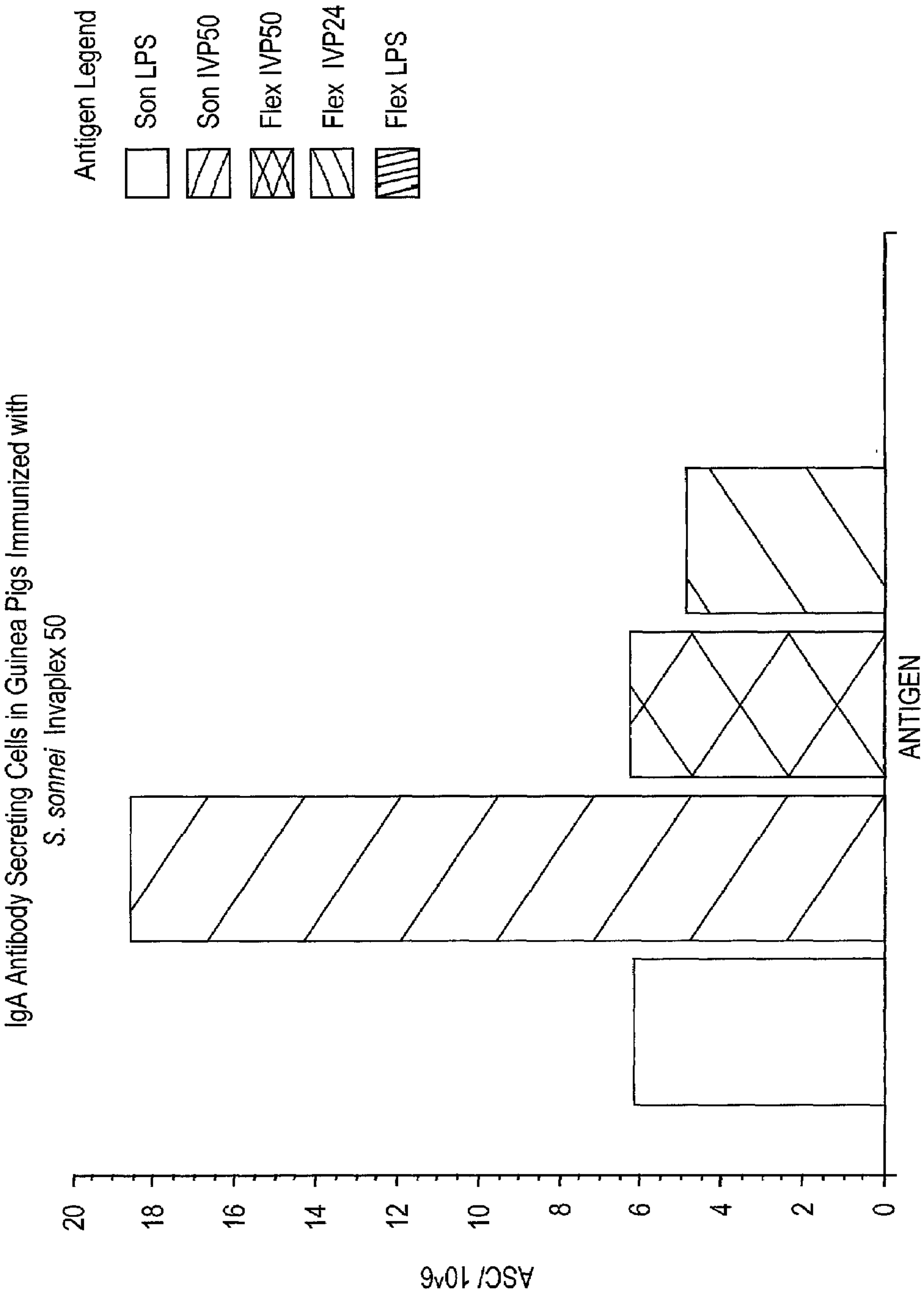
FIG. 14. IgA antibody secreting cells (ASC) in guinea pigs immunized with *S. sonnei* Invaplex 50. Peripheral blood lymphocytes (PBL) from guinea pigs immunized with 3 intranasal doses (25 μg) of *S. sonnei* Invaplex 50, given at two-week intervals, were incubated with various *Shigella* antigens to determine the number of circulating B-cells secreting IgA to the various *Shigella* antigens. Blood was collected one week after the final immunization. The number of ASC per 1 million cells is presented. The PBLs were incubated with 5 different *Shigella* antigens including *S. sonnei* LPS (Son LPS), *S. sonnei* Invaplex 50 (Son IVP50), *S. flexneri* Invaplex 50 (Flex IVP50), *S. flexneri* Invaplex 24 (Flex IVP24), and *S. flexneri* LPS (Flex LPS).

Peripheral blood lymphocytes (PBL) from guinea pigs immunized with 3 intranasal doses (25 μg) of *S. sonnei* Invaplex 50, given at two-week intervals, were incubated with various *Shigella* antigens to determine the number of circulating B-cells secreting IgA to the various *Shigella* antigens. Blood was collected one week after the final immunization. The number of ASC per 1 million cells is presented. The PBLs were incubated with 5 different *Shigella* antigens including *S. sonnei* LPS (Son LPS), *S. sonnei* Invaplex 50 (Son IVP50), *S. flexneri* Invaplex 50 (Flex IVP50), *S. flexneri* Invaplex 24 (Flex IVP24), and *S. flexneri* LPS (Flex LPS). Guinea pigs immunized with *S. sonnei* Invaplex 50 produce antibody secreting cells (ASC) that secrete antibodies to *S. sonnei* LPS and *S. sonnei* Invaplex 50 but also to *S. flexneri* Invaplex 50 and *S. flexneri* Invaplex 24, but not to *S. flexneri* LPS (FIG. 14). This supports our data indicating that *S. sonnei* Invaplex 50 stimulates a heterologous immune response.

EXAMPLE 4

Cross-Reactive Antigens Common to Invaplex 50 from all *Shigella* spp and Enteroinvasive *E. coli.*

Immune serum from a guinea pig (GP 6LH) immunized with *S. sonnei* Invaplex 50 and subsequently challenged with *S. sonnei*, was used in a western blot (FIG. 15) to probe Invaplex 24 and Invaplex 50 preparations from *S. flexneri* 2a, *S. sonnei* (Mosley), *S. dysenteriae* 1, *S. boydii* 2 and enteroinvasive *E. coli* (lanes are labeled with antigen content). Each lane of this western blot was loaded with 15 μg of the indicated Invaplex. The GP 6LH antiserum contains antibodies to several *Shigella* proteins, including IpaB, IpaC, 84 kDa, 72 kDa, 70 kDa, 64 kDa, and 58 kDa proteins. Whole cell lysates of *S. flexneri* 5 Vir+ and *S. flexneri* 5 Vir− are in the left two lanes of the blot. The extreme left lane contains pre-stained molecular size standards (MW Markers). The proteins samples were initially separated on a 9% acrylamide gel prior to blotting. *Shigella* antigens are indicated with arrows on the right hand side of the blot.

EXAMPLE 5

Cross-Reactive Antigens Common to Invaplex 50 from all *Shigella* spp and Enteroinvasive *E. coli.*

Immune serum from a guinea pig (GP 6RS) immunized with *S. flexneri* Invaplex 50 and subsequently challenged with *S. flexneri* 2a, was used in a western blot (FIG. 16) to probe Invaplex 24 and Invaplex 50 preparations from *S. flexneri* 2a, *S. sonnei* (Mosley), *S. dysenteriae* 1, *S. boydii* 2 and enteroinvasive *E. coli* (lanes are labeled with antigen content). Each lane of this western blot was loaded with 15 μg of the indicated Invaplex. The GP 6RS antiserum contains antibodies to several *Shigella* proteins, including IpaB, IpaC, 84 kDa, 72 kDa, 70 kDa, 64 kDa, and 58 kDa proteins. Whole cell lysates of *S. flexneri* 5 Vir+ and *S. flexneri* 5 Vir− are in the left two lanes of the blot. The extreme left lane contains pre-stained molecular size standards (MW Markers). The proteins samples were initially separated on a 9% acrylamide gel prior to blotting. *Shigella* antigens are indicated with arrows on the right hand side of the blot.

EXAMPLE 6

*S. sonnei* invaplex 50 stimulates antibodies which recognize protein antigens present in All *Shigella* species and enteroinvasive *E. coli.*

Serum collected from a guinea pig immunized with *S. sonnei* Invaplex 50 and subsequently challenged with *S. sonnei*, was used in a western blot (FIG. 17) to probe various *Shigella* strains for the presence of the 84 kDa and 72 KDa proteins. Whole cell lysates (WCL) were electrophoresed, blotted to nitrocellulose and then reacted with the antiserum. Each lane contains a different strain of *Shigella* as indicated above the lane. Both virulent (Vir+) and avirulent (Vir−) *Shigella* strains were used. The Vir+ plus strains express IpaB, IpaC and IpaD. Vir− strains do not express the Ipa proteins. Two lanes just left of the molecular weight marker contain purified Invaplex 24 and Invaplex 50 from *S. flexneri* 2a. The two lanes (*S. flexneri* 5 Vir+ WCL and *S. flexneri* 5 Vir− WCL) on the extreme right-hand side of the gel were probed with a monoclonal antibody mixture that specifically recognizes IpaB and IpaC. These controls clearly indicate where IpaB and IpaC are located on these gels. Molecular weight standards are indicated by the 97, 43, 30 and 18 kDa sizes. Arrows point to the specific proteins 84 kDa, 72 kDa, IpaB and IpaC.

EXAMPLE 7

*S. flexneri* 2a Invaplex 50 stimulates antibodies, which recognize protein antigens present in all *Shigella* species and enteroinvasive *E. coli.*

Serum collected from a guinea pig immunized with *S. flexneri* 2a Invaplex 50 and then challenged with *S. flexneri* 2a, was used in a western blot (FIG. 18) to probe various *Shigella* strains for the presence of the 84 kDa and 72 KDa proteins. Whole cell lysates (WCL) were electrophoresed, blotted to nitrocellulose and then reacted with the antiserum. Each lane contains a different strain of *Shigella* as indicated above the lane. Both virulent (Vir+) and avirulent (Vir−) *Shigella* strains were used. The Vir+ plus strains express IpaB, IpaC and IpaD. Vir− strains do not express the Ipa proteins. Two lanes just left of the molecular weight marker contain purified Invaplex 24 and Invaplex 50 from *S. flexneri* 2a. The two lanes (*S. flexneri* 5 Vir+ WCL and *S. flexneri* 5 Vir− WCL) on the extreme right-hand side of the gel were probed with a monoclonal antibody mixture that specifically recognizes IpaB and IpaC. These controls clearly indicate where IpaB and IpaC are located on these gels. Molecular weight standards are indicated by the 97, 43, 30 and18 kDa sizes. Arrows point to the specific proteins 84 kDa, 72 kDa, IpaB and IpaC.

EXAMPLE 8

Identification of Cross-Reactive Protein Antigens of Invaplex 50 on the Surface of Shigellae.

Using surface affinity-purification of antibodies to purify antibodies reactive with antigens localized on the surface of shigellae, it has been possible to identify the newly described antigens found in Invaplex 50 of *Shigella sonnei* and *S. flexneri* as having epitopes accessible on the surface of the bacterium. Such surface-exposed antigens are likely targets for antibody mediated killing or clearing of bacteria in an infected host.

Figure 19:
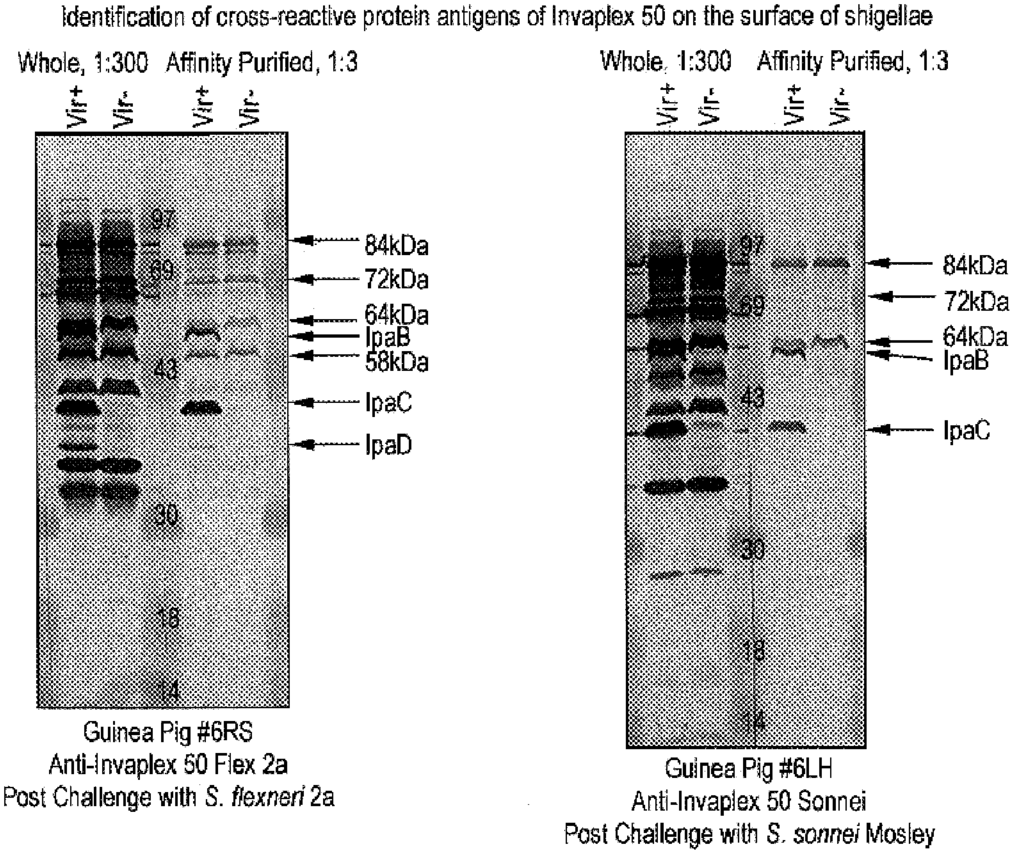
FIG. 19. Identification of cross-reactive protein antigens of Invaplex 50 on the surface of shigellae. The surface proteins were identified by incubating convalescent antiserum containing antibodies to the 84 kDa and the 72 kDa proteins (along with antibodies to other protein antigens as well) with whole, intact, virulent shigellae. After a short incubation and washing to remove non-specifically bound antibodies, the antibodies bound to surface antigens were eluted with a low-pH glycine buffer. The eluted antibody solution was neutralized to pH 7.4 and subsequently used in western blots. Lanes under "Affinity-purified, 1:3"; the left lane is a whole cell lysate of virulent *S. flexneri* 5 strain M90T-W, the right lane is a whole cell lysate of avirulent *S. flexneri* 5 strain M90T-55. Lanes under "whole, 1:300"; the left lane is a whole cell lysate of virulent *S. flexneri* 5 strain M90T-W, the right lane is a whole cell lysate of avirulent *S. flexneri* 5 strain M90T-55. Essentially the same set of surface protein antigens were recognized by affinity-purified antisera obtained from guinea pigs immunized with either *S. flexneri* Invaplex 50 (left hand panel) or *S. sonnei* Invaplex 50 (right-hand panel). The middle lane in each panel is a molecular weight marker with the size (in kDa) of the standards indicated.
Figure 20A:
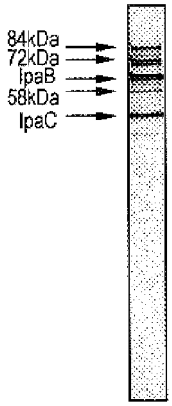
FIGS. 20A, B C and D. Characterization of the high molecular mass complex isolated from *Shigella* Invaplex 50 (HMMC-50). The high molecular mass complex (HMMC) is isolated from Invaplex preparations by size exclusion chromatograph. Panel A, shows a western blot of *Shigella* HMMC-50 probed with anti-*S. sonnei* Invaplex 50 guinea pig sera. This anti sera reacts with the 84 kDa, 72 kDa, IpaB, 58 kDa, and IpaC bands present in the HMMC-50. Panel B is a western blot of HMMC-50 that was probed with monoclonal antibodies to IpaB and IpaC. The IpaB and IpaC bands are indicated. Panel C is a silver stained gel of proteinase-K treated HMMC-50 which shows a typical LPS banding pattern. Panel D shows the right-hand blot, which contains three strips with HMMC-50 from S. sonnei that were incubated with sera from a guinea pig (6LH) immunized with S. sonnei Invaplex 50. Three sera are used, the pre-immunization serum (Pre), the post-immunization serum (Post Immun) and serum from the immunized guinea pig after it was challenged with Shigella. The last strip on the right-hand side contains whole cell lysates of virulent shigellae (*S. flexneri* 5 vir + (left lane) and *S. flexneri* 5 vir- (right lane)). This strip was reacted with a monkey convalescent serum which reasts with IpaA, IpaB, IpaC and IpaD.
Figure 20B:
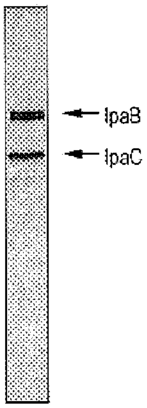
Figure 20C:
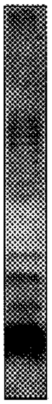
Figure 20D:
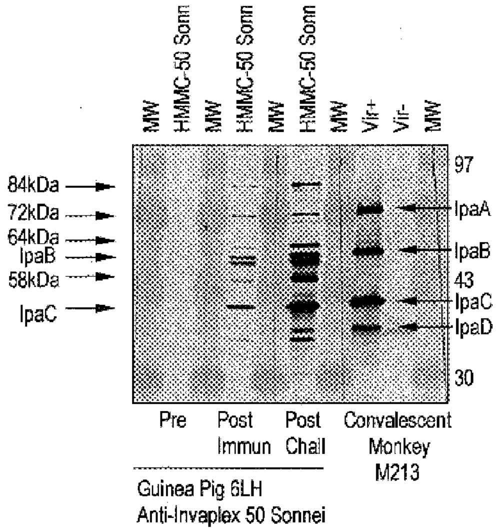

The surface proteins were identified by incubating convalescent antiserum containing antibodies to the 84 kDa and the 72 kDa proteins (along with antibodies to other protein antigens as well) with whole, intact, virulent shigellae. After a short incubation and washing to remove non-specifically bound antibodies, the antibodies bound to surface antigens were eluted with a low-pH glycine buffer. The eluted antibody solution was neutralized to pH 7.4 and subsequently used in western blots (FIG. 19). In the blots, any protein band that was recognized by the affinity-purified sera was considered surface-exposed. The western blots (lanes under "Affinity-purified, 1:3"; the left lane is a whole cell lysate of virulent *S. flexneri* 5 strain M90T-W, the right lane is a whole cell lysate of avirulent *S. flexneri* 5 strain M90T-55) in FIG. 19 indicate that the 84 kDa, 72 kDa, 64 kDa, IpaB, and IpaC were exposed on the *Shigella* surface. Several proteins, recognized by antibodies in the antiserum before affinity-purification (see 2 lanes under "whole, 1:300"; the left lane is a whole cell lysate of virulent *S. flexneri* 5 strain M90T-W, the right lane is a whole cell lysate of avirulent *S. flexneri* 5 strain M90T-55), were not recognized by the affinity-purified serum, indicating that epitopes on these proteins were not exposed on the *Shigella* surface and thus not collected by the affinity purification technique. Essentially the same set of surface protein antigens were recognized by affinity-purified antisera obtained from guinea pigs immunized with either *S. flexneri* Invaplex 50 (left hand panel) or *S. sonnei* Invaplex 50 (right-hand panel). The middle lane in each panel is a molecular weight marker with the size (in kDa) of the standards indicated.

EXAMPLE 9

Characterization of the High Molecular Mass Complex Isolated from *Shigella* Invaplex 50 (HMMC-50).

The high molecular mass complex (HMMC) is isolated from Invaplex preparations by size exclusion chromatography. FIG. 20, panel A, shows a western blot of *Shigella* HMMC-50 probed with anti-*S. sonnei* Invaplex 50 guinea pig sera. This antisera reacts with the 84 kDa, 72 kDa, IpaB, 58 kDa, and IpaC bands present in the HMMC-50. FIG. 20, panel B is a western blot of HMMC-50 that was probed with monoclonal antibodies to IpaB and IpaC. The IpaB and IpaC bands are indicated. FIG. 20, panel C is a silver stained gel of proteinase-K treated HMMC-50 which shows a typical LPS banding pattern.

Figure 17:
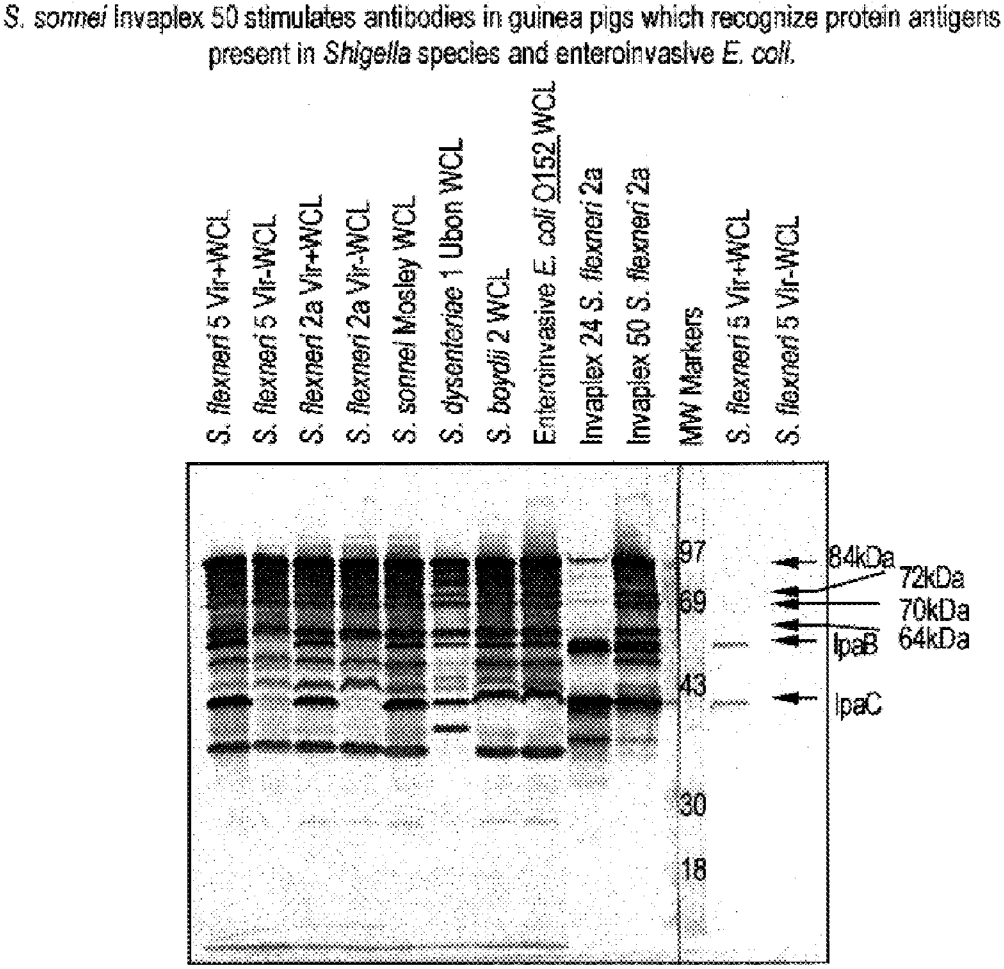
FIG. 17. *S. sonnei* Invaplex 50 stimulates antibodies which recognize protein antigens present in all *Shigella* species and enteroinvasive *E. coli*. Serum collected from a guinea pig immunized with *S. sonnei* Invaplex 50 and subsequently challenged with *S. sonnei*, was used in a western blot to probe various *Shigella* strains for the presence of the 84 kDa and 72 KDa proteins. Whole cell lysates (WCL) were electrophoresed, blotted to nitrocellulose and then reacted with the antiserum. Each lane contains a different strain of *Shigella* as indicated above the lane. Both virulent (Vir+) and avirulent (Vir−) *Shigella* strains were used. The Vir+ plus strains express IpaB, IpaC and IpaD. Vir− strains do not express the Ipa proteins. Two lanes just left of the molecular weight marker contain purified Invaplex 24 and Invaplex 50 from *S. flexneri* 2a. The two lanes (*S. flexneri* 5 Vir+ WCL and *S. flexneri* 5 Vir− WCL) on the extreme right-hand side of the gel were probed with a monoclonal antibody mixture that specifically recognizes IpaB and IpaC. These controls clearly indicate where IpaB and IpaC are located on these gels. Molecular weight standards are indicated by the 97, 43, 30 and 18 kDa sizes. Arrows point to the specific proteins 84 kDa, 72 kDa, IpaB and IpaC.
Figure 18:
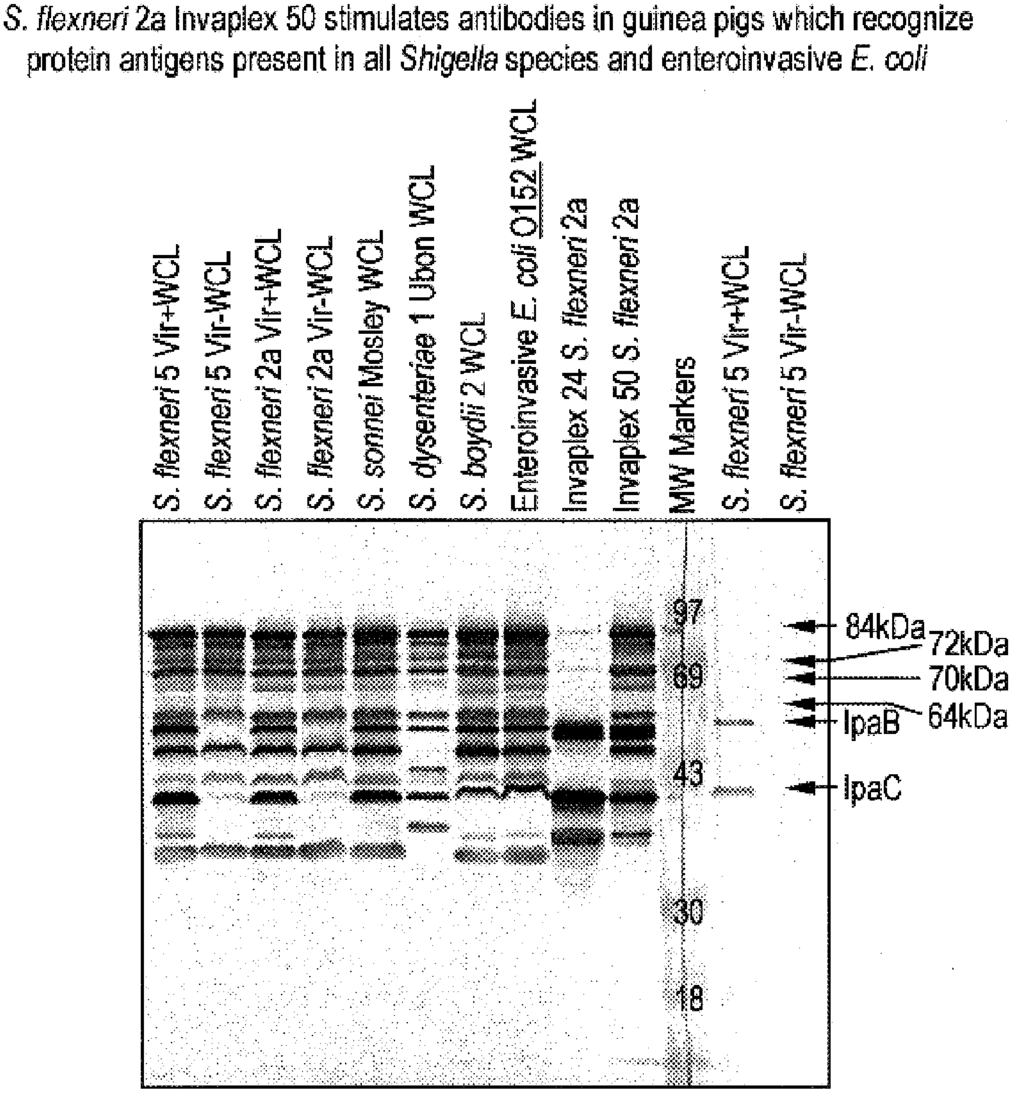
FIG. 18. *S. flexneri* 2a Invaplex 50 stimulates antibodies, which recognize protein antigens present in all *Shigella* species and enteroinvasive *E. coli*. Serum collected from a guinea pig immunized with *S. flexneri* 2a Invaplex 50 and then challenged with *S. flexneri* 2a, was used in a western blot to probe various *Shigella* strains for the presence of the 84 kDa and 72 KDa proteins. Whole cell lysates (WCL) were electrophoresed, blotted to nitrocellulose and then reacted with the antiserum. Each lane contains a different strain of *Shigella* as indicated above the lane. Both virulent (Vir+) and avirulent (Vir−) *Shigella* strains were used. The Vir+ plus strains express IpaB, IpaC and IpaD. Vir− strains do not express the Ipa proteins. Two lanes just left of the molecular weight marker contain purified Invaplex 24 and Invaplex 50 from *S. flexneri* 2a. The two lanes (*S. flexneri* 5 Vir+ WCL and *S. flexneri* 5 Vir− WCL) on the extreme right-hand side of the gel were probed with a monoclonal antibody mixture that specifically recognizes IpaB and IpaC. These controls clearly indicate where IpaB and IpaC are located on these gels. Molecular weight standards are indicated by the 97, 43, 30 and 18 kDa sizes. Arrows point to the specific proteins 84 kDa, 72 kDa, IpaB and IpaC.

The unexpected findings of heterologous immunity induced by the *S. sonnei* Invaplex 50 will be expanded upon. These studies will attempt to identify the key antigens responsible for the heterologous immunity. *S. sonnei* Invaplex 50 and *S. flexneri* Invaplex 50 induced antibodies cross-reactive with all *Shigella* species (FIGS. 17, 18, and 20). The specificity of this serum include antibodies to IpaB, IpaC, 84 kDa, 72 kDa, 64 kDa and the 58 kDa proteins. At the present time, candidate proteins include the Ipa proteins and also the 72 kDa and 84 kDa polypeptides. In addition, using antibodies affinity-purified against *Shigella* surface antigens, the following proteins were localized to the *Shigella* surface: IpaB, IpaC, 84 kDa, 72 kDa and the 64 kDa proteins. The presence of the invasins and other proteins almost exclusively in the HMMC of the Invaplex, provides a means by which these proteins can be isolated for study.

What is claimed is:

1. A method for providing a protective immune response in a subject in need of protection against Shigellosis caused by a first *Shigella* species comprising mucosally administering to the subject a vaccine comprising an isolated *Shigella* Invaplex 50, which contains LPS, IpaB, IpaC, IpaD, VirG 72 kDa and 84 kDa polypeptides, to induce a protective immune response against the first *Shigella* species, wherein the *Shigella* source for the Invaplex 50 is distinct from the first *Shigella* species and said administration is selected from the group consisting of oral, rectal, and intranasal.

2. A method comprising 1) administering to a subject a composition comprising an isolated *Shigella* Invaplex 50, which contains LPS, IpaB, IpaC, IpaD, VirG 72 kDa and 84 kDa polypeptides and 2) challenging the subject with a *Shigella* species which is a different species than the Invaplex 50 source wherein the *Shigella* Invaplex 50 source is selected from the group consisting of *S. flexneri, S. sonnei, S. boydii*, and *S. dysenteriae*, and an invasive bacteria is selected from *S. flexneri, S. sonnei, S. Boydii*, or *S. Dysenteriae.*

3. The method according to claim 2 further compring measuring for a protective immune response.

* * * * *